United States Patent [19]
Schwankhart

[11] Patent Number: 5,909,884
[45] Date of Patent: Jun. 8, 1999

[54] PROCESS AND APPARATUS FOR CONTINUOUS PRODUCTION OF LENGTH PORTIONS FROM A STRAND OF FLUID-ABSORBING MATERIAL

[76] Inventor: Gerhard Schwankhart, Tuffeltsham 68, A-4800, Attnang-Puchheim, Austria

[21] Appl. No.: 08/945,578
[22] PCT Filed: Apr. 26, 1996
[86] PCT No.: PCT/EP96/01753
  § 371 Date: Jan. 14, 1998
  § 102(e) Date: Jan. 14, 1998
[87] PCT Pub. No.: WO96/33682
  PCT Pub. Date: Oct. 31, 1996

[30] Foreign Application Priority Data

Apr. 27, 1995 [DE] Germany ............................. 19515517

[51] Int. Cl.⁶ .................................................. A61F 13/20
[52] U.S. Cl. ................................................ 28/118; 28/116
[58] Field of Search ........................... 28/118, 119, 120, 28/116, 117, 121, 126, 130, 134

[56] References Cited

U.S. PATENT DOCUMENTS 4,498,218  2/1985  Friese ........................................ 28/118
5,165,152  11/1992  Kramer et al. ............................. 28/118
5,592,725  1/1997  Brinker ..................................... 28/118

FOREIGN PATENT DOCUMENTS 261771  1/1949  Switzerland .............................. 28/118
355255  8/1961  Switzerland .............................. 28/118
9007314  7/1990  WIPO ....................................... 28/118

*Primary Examiner*—John J. Calvert
*Assistant Examiner*—Larry D. Worrell, Jr.
*Attorney, Agent, or Firm*—Joel A. Rothfus

[57] ABSTRACT

Process for the production of longitudinally extending pressed absorption bodies from an endless nonwoven web which is transported continuously in the direction of advance by pressing elements drivable in the direction of rotation and belonging to a pressing station and which is provided simultaneously with at least three longitudinal grooves arranged at equal angular spacings, whereupon the nonwoven web forming a pressed strand is subdivided into portions of specific length, characterized in that the nonwoven web (140) is driven in the conveying direction (x), by means of the pressing elements drivable in the direction of rotation, in a plane extending transversely relative to its longitudinal direction and simultaneously is pressed radially at least to the final cross-section of a pressed strand (240) and, at the same time, is provided with longitudinal grooves (131).

29 Claims, 20 Drawing Sheets

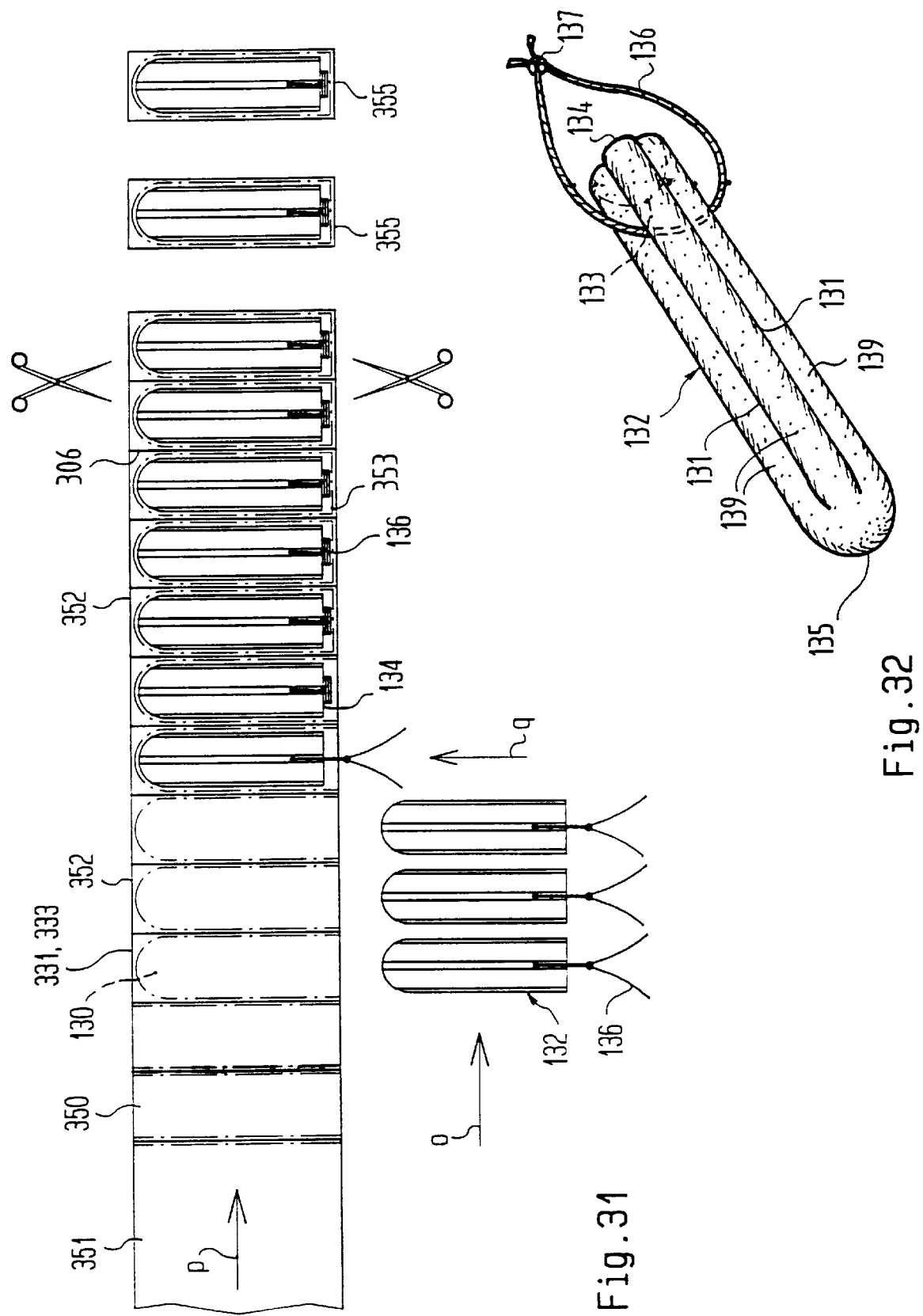

PROCESS AND APPARATUS FOR CONTINUOUS PRODUCTION OF LENGTH PORTIONS FROM A STRAND OF FLUID-ABSORBING MATERIAL

The invention relates to a process and an apparatus for the continuous production of length portions from a strand of fluid-absorbing material, the material strand being shaped into a pressed strand by the pressing in of longitudinal grooves at equal circumferential angular spacings by means of press elements drivable in the direction of rotation and simultaneously being transported in the run-through direction as well as subsequently being subdivided into length portions by movable severing elements.

A process and an apparatus of the abovementioned generic type are known from WO 90/07314. According to this document, a multi-layer fibre-material web is folded on itself by means of a plurality of longitudinal folds and is rounded in cross-section. The fibre-material web is thereafter surrounded with a wrapping band, the longitudinal edges of which are sealed. The fibre-material web is subsequently rolled down in steps, at least to the cross-section of an absorption body, in a roller frame by means of a multiplicity of pairs of rollers offset relative to one another in the circumferential direction, and a nonwoven strand is formed. During this reduction in cross-section of the fibre-material web by means of the said pairs of rollers, the nonwoven strand is provided with four longitudinal grooves. The nonwoven strand can be heated during the press-rolling. Length portions corresponding to the absorption bodies are subsequently pre-severed, with the exception of the thin connecting web, by nip-rolling, the ends of these length portions acquiring the form of a hump and a dip respectively, before they are separated completely. Thereafter, a recovery tape can be fastened to the rear end of the absorption body, in order to complete a tampon for feminine hygiene.

Swiss Patent Specification 261,771 discloses a process and a machine for the production of a wrapped tampon consisting of a plurality of angular fluid-absorbing disks, such as cotton wadding, which, stacked centrically, are folded up to form a cup and are pressed into the form of a peg. The disk stack is pressed by means of a ram into a tube which tapers conically at the start and which is mounted fixedly on a table. Provided on the tube circumference is a plurality of longitudinal slots, through each of which projects the circumference of a freely rotatable disk fastened to supporting arms screwed to the table. During the piercing of the cup by the tube, these disks are rotated, and folds or flutes are formed. Subsequently, a heatable cylindrical die, having inner longitudinal ribs which are aligned with the disks and which further indent the flutes, is used. Thereafter, the die has to be removed from the table and placed over a pressing member, the convex surface of which projects, in this position, into the lower end of the die. An axially acting pressing member having a concave surface is then pressed into the upper end of the die, so that, in the course of the dwell time in the die, the peg is provided on the one hand with a finger dip and on the other hand with a round hump.

Swiss Patent Specification 355 255 describes a longitudinally stretchable menstruation tampon with recovery tape as well as a fully automatic process and apparatus for the production of this, the absorbent tampon body being surrounded completely by a wrapping made of moisture-permeable material. The tampon consists of a length portion of a multi-layer wadding web folded in the longitudinal centre, the folding point forming the rear end of the tampon body. The tampon body is surrounded by a hydrophilic gauze, of which the two ends projecting above the folding point serve as recovery means. The gauze is fastened to the end of the tampon by means of a binder. The tampon body is pressed laterally to form a cylindrical tampon in a press die having a stationary and a movable press mould, each semi-cylindrical, and is subsequently provided with a round hump at the front end by axial pressing. The known apparatus contains a curved guide channel for folding the wadding web round to half width, an advancing and shaping wheel projecting from above into the folding channel and pressing the folding point of the web onto the channel bottom. For laying on and folding the gauze web above the guide channel, there are provided a guide roller and a double-flange wheel, the flanges of which engage over the guide channel closed at this point. The wadding web together with the gauze web fastened to it is rotated through 90° on a table by means of two folding-round rollers and is subsequently fed by two driven press rollers to a circular knife for severing tampon blanks which are thereafter transported to the tampon press.

The object on which the invention is based is to improve the process and apparatus according to the pre-characterizing clause of the present independent patent claims relating respectively to them, in such a way that absorption bodies made of a multi-layer web of absorbent material being folded or wound about its longitudinal axis can be produced continuously and reliably at a comparatively low outlay and at a high production speed.

The invention achieves this object by means of the characterizing clause of the present independent patent claims relating respectively to the process and to the apparatus.

It was found, surprisingly, that such a strand of a multi-layer web, in a single operation, can be pressed, at least to the final dimension of the absorption body, in only one plane transverse to its direction of transport, merely by exerting a linear radial pressing force on generatrices of the nonwoven strand and, at the same time, synchronous motive forces by which said web can be continuously further transported simultaneously as a finished pressed strand at an extremely high speed and be processed to the desired final product in further stations.

The apparatus according to the invention for carrying out the process according to the invention for the production of absorption bodies accordingly consists of a disk press having at least three essentially circular press disks which are arranged on a supporting stand essentially radially to the axis of the disk press in a common plane oriented perpendicularly to the direction of transport of the disk press, the press disks being connected to a drive motor and to a device by means of which the press disks are adjustable radially to the axis of the disk press and in the direction of the press-disk axes.

The invention is explained in more detail below by means of the diagrammatic drawing of an exemplary embodiment of a high-speed apparatus for the continuous production of length portions from a pressed nonwoven strand. In this:

FIGS. 30 and 31 show an apparatus for the packaging of absorption bodies; and

FIG. 32 shows a finished absorption body in perspective view.

The drawings illustrate a high-speed apparatus for the continuous production, machining and packaging of absorption bodies made from a pressed nonwoven web, which, in particular, allows the processing of compressible, biologically degradable natural materials, such as natural fibre material, for example consisting of cotton fibres or other cellulose-containing fibres, sponge, etc. Articles of this type are, for example, absorption bodies for hygienic purposes, especially for feminine hygiene, cleaning purposes, for example for cleaning appliances which are used industrially or domestically, or for sealing-off purposes, for example in windows or doors which, if appropriate, are impregnated with a biologically degradable sealing agent.

Figure 1:
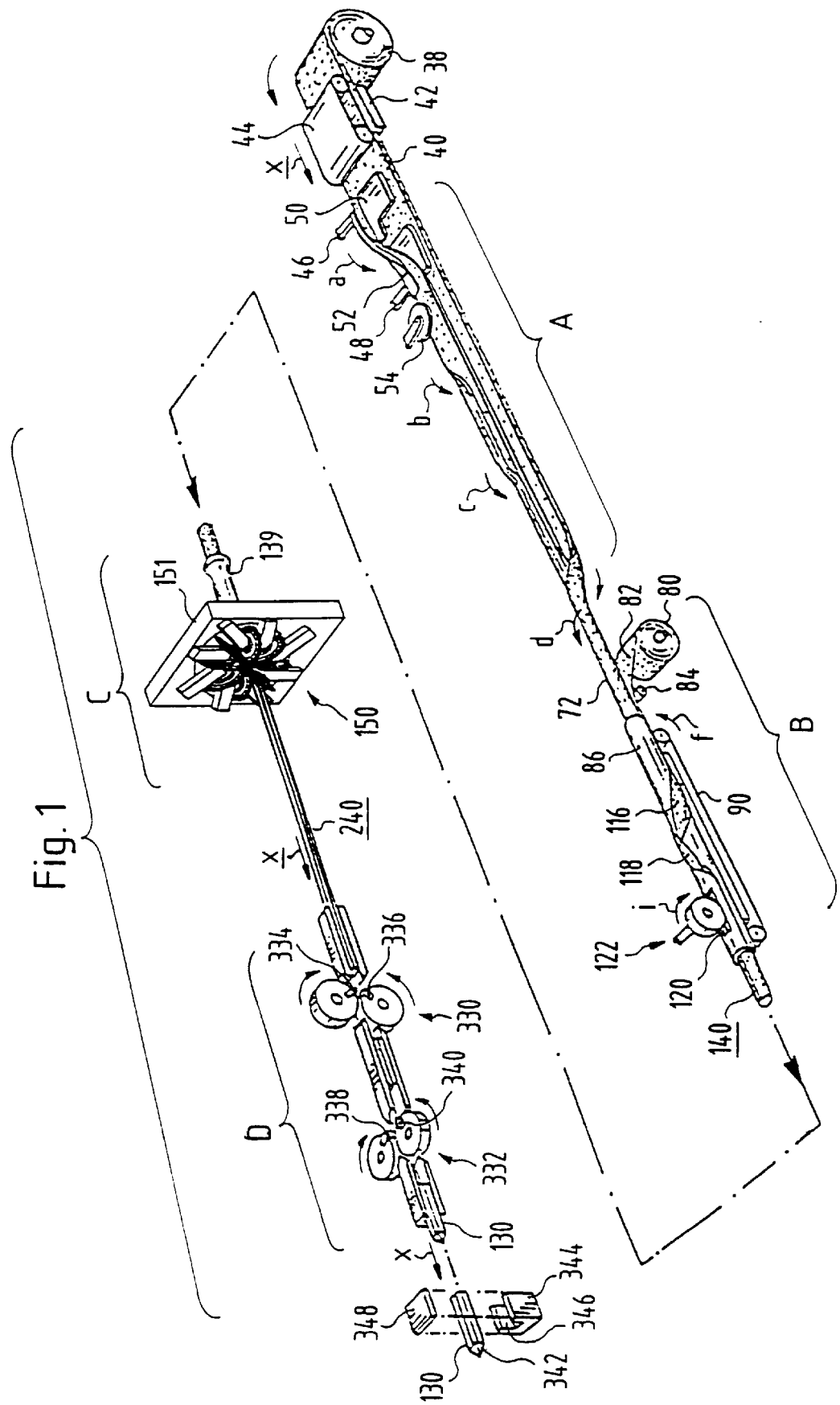
FIG. 1 shows a perspective, partially diagrammatic view of the apparatus according to the invention, with folding, wrapping-band attachment, pressing and severing stations.

FIG. 1 shows an apparatus for the continuous production of absorption bodies 130, in the present case of tampon blanks, from each of which there is formed a tampon 132 for feminine hygiene which, as shown in FIG. 32, is provided at its front end with a round hump 135, on the circumference with eight longitudinal grooves 131 and eight longitudinal ribs 139 and at its rear end 134 with a finger dip 133 as an introduction aid, and finally with a recovery tape 136, the ends of which are connected by means of a knot 137.

According to FIG. 1, the apparatus consists of a stock roll 38 for a nonwoven web 40 which is processed continuously in stations connected in series, namely a folding station A, a wrapping-band attachment station B, a pressing station C and a severing station D which, with the exception of the pressing station C, are described essentially in WO 90/07314.

Folding Station

It is evident from FIG. 1 that, in the direction of advance of an arrow x of the nonwoven web 40, a stationary guide plate 42 for the endless nonwoven web 40 is arranged behind the stock roll 38. Mounted above the guide plate 42 at a distance is an endless conveyor belt 44 which is preferably vertically adjustable and which, by means of frictional connection, causes the nonwoven web 40 to be conveyed continuously in the direction of the arrow x. In contrast to the embodiment shown, an endless conveyor belt can also be provided instead of the guide plate 42, in which case at least one of the conveyor belts is drivable. These devices as well as the stations described below and the devices associated with them are arranged on a stand, of which only stand parts 46 and 48 are indicated. Furthermore, it goes without saying that the guide plate 42 extends at least over a substantial part of the underside of the folding station A and is merely indicated in FIG. 1 for the sake of clarity.

Arranged above the nonwoven web 40, behind the conveyor belt 44 in the direction of advance x, is a baffle plate 50, behind which is located a folding plate 52 followed by a rotatable folding disk 54. By means of this first folding plate 52, a longitudinal side 56 of the nonwoven web 40 on the right in the direction of movement x is subjected, according to FIG. 2, to a first folding operation I. At the same time, the longitudinal side 56 of the nonwoven web 40 on the right in the direction of movement x is folded round upwards parallel to the longitudinal direction of the nonwoven web 40 in the direction of an arrow a and is laid onto the top side of the nonwoven web 40. It is evident from FIGS. 2 and 3 that, after the folding operation I, a right-hand longitudinal edge 58 assumes a greater distance from a left-hand longitudinal edge 60 than the longitudinal mid-axis of the nonwoven web 40. In the present exemplary embodiment, the nonwoven web 40 has a width of 25 cm. In this case, the width of a first fold 62 expediently amounts to 9 cm. Depending on the intended use of the particular absorption bodies 130 produced, the dimensions of the nonwoven web 40 can be made to vary greatly. As a rule, however, the width of the nonwoven web 40 will be in the range between 15 and 40 cm.

Figure 2:
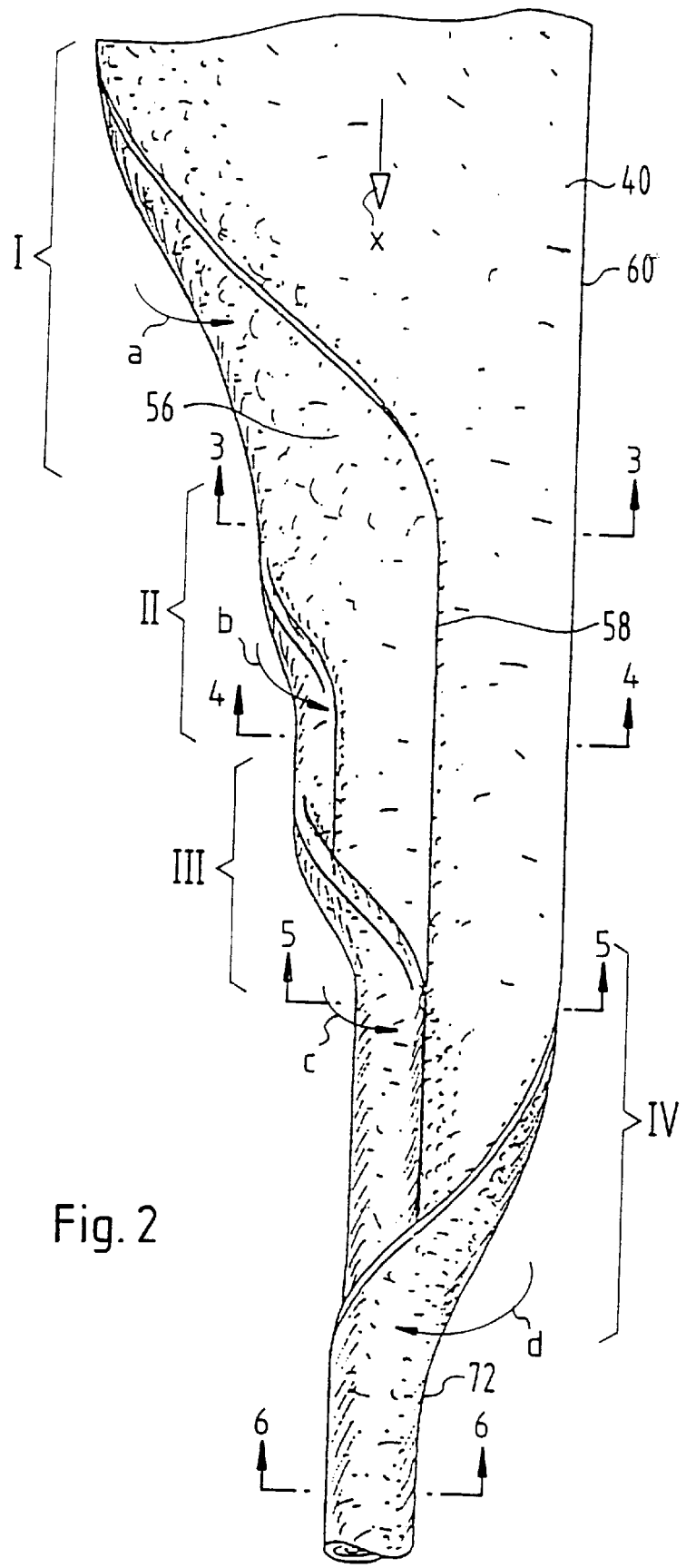
FIG. 2 shows a top view of the folding pattern of the nonwoven web.
Figure 3:
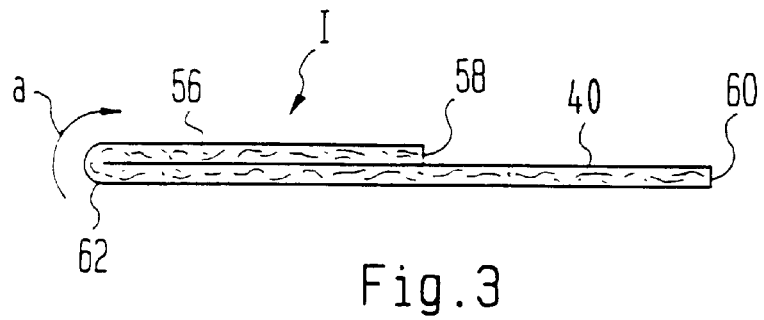
FIG. 3 shows a cross-section along the line 3—3 in FIG. 2, which shows the first folding of the nonwoven web.
Figure 4:
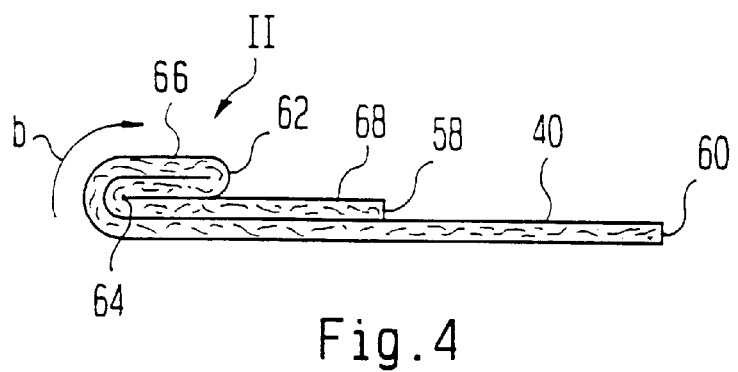
FIG. 4 shows a cross-section along the line 4—4 in FIG. 2, which shows the second folding of the nonwoven web.

With further reference to FIGS. 1, 2 and 4, it is evident that the first folding operation I is followed by a second folding operation II which, again, is carried out by means of suitable folding plates and folding rollers, although these are not shown in detail for the sake of clarity in the drawing. In this folding operation II, the right-hand longitudinal edge 58 formed by the first fold 62 is folded round in the direction of an arrow b onto the folded-round right-hand longitudinal side 56 about a longitudinal fold 64 onto the top side of the longitudinal side 56 and is laid approximately onto the middle third of the width of the longitudinal side 56. With the said width of the nonwoven web 40, this second folding takes place over a width of approximately 2 cm.

Figure 5:
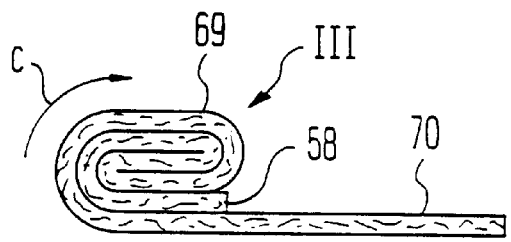
FIG. 5 shows a cross-section along the line 5—5 in FIG. 2, which shows the third folding of the nonwoven web.

As is evident from FIGS. 1, 2, 4 and 5, there follows a folding operation III, in which a four-layer bundle 66 is folded round in the direction of an arrow c onto a still uncovered part 68 of the right-hand longitudinal side 56, to the left according to FIG. 5, as seen in the direction of movement x of the nonwoven web 40, so that the nonwoven web 40 is now limited by a six-layer bundle 69 on its right-hand side in the direction of movement x. With the said width of the nonwoven web 40, this folding operation III extends over approximately 3.5 cm.

Figure 6:
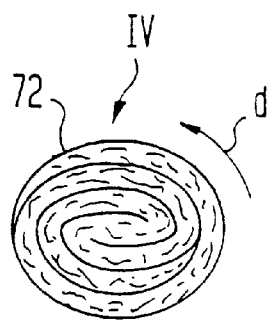
FIG. 6 shows a cross-section along the line 6—6 in FIG. 2, which shows the folded nonwoven web after a side edge has been folded round onto the top side of the folded part of the nonwoven web.

A left-hand longitudinal side 70 of the nonwoven web 40, still remaining according to FIG. 5, is then folded round the left-hand edge of the six-layer bundle 69 onto the top side of the latter in the opposite direction according to arrow d in FIGS. 1, 2 and 6, as seen in the direction of movement x of the nonwoven web 40, so that this folding operation IV forms a seven-layer nonwoven web 72 which is surrounded completely by the remaining left-hand longitudinal side 70 of the nonwoven web 40. Provided at the end of the folding station A are profiled rollers which impart the round cross-section according to FIG. 6 to the seven-layer nonwoven web 72. Press rollers of this type are known and are therefore not shown. Before the execution of the folding operation IV, the left-hand longitudinal side 70 of the nonwoven web 40 has approximately a width of 6 cm. Depending on the particular intended use of the absorption body, of course, another type of longitudinal folding or layering of the nonwoven web 40 can also be carried out.

Wrapping-band attachment station

It can be seen from FIG. 1 that the wrapping-band attachment station B has a stock roll 80 for a wrapping band 82 in the region of the completely layered and rounded nonwoven web 72. The wrapping band 82 is fluid-permeable, and may have a hydrophobic finish. The wrapping band 82 may be an apertured plastic film, a reticulated plastic film, a nonwoven fabric, a knitted fabric, or the like. The wrapping band 82 preferably possesses, at least partially, thermoplastic constituents to enable it to be thermally bonded. The thermoplastic constituents may be fibrous or powdered. The wrapping band 82 may also be adhesively bonded, ultrasonically bonded, and the like. Useful wrapping band 82 materials and bonding mechanisms will be recognized by those ordinarily skilled in the art.

Preferably, the wrapping band 82 consists of a nonwoven fibre layer (nonwoven) which has thermoplastic constituents. This wrapping band 82 is made wider than the circumference of the nonwoven web 72. A guide roller 84 is arranged transversely to the direction of movement x behind the stock roll 80 and at a short distance underneath the nonwoven web 72. According to FIG. 7, this guide roller 84 has the function of guiding the wrapping band 82, supplied from the stock roll 80 in the direction of arrow d into a direction e approximately parallel to the nonwoven web 72, and under a guide tube 86.

Figure 7:
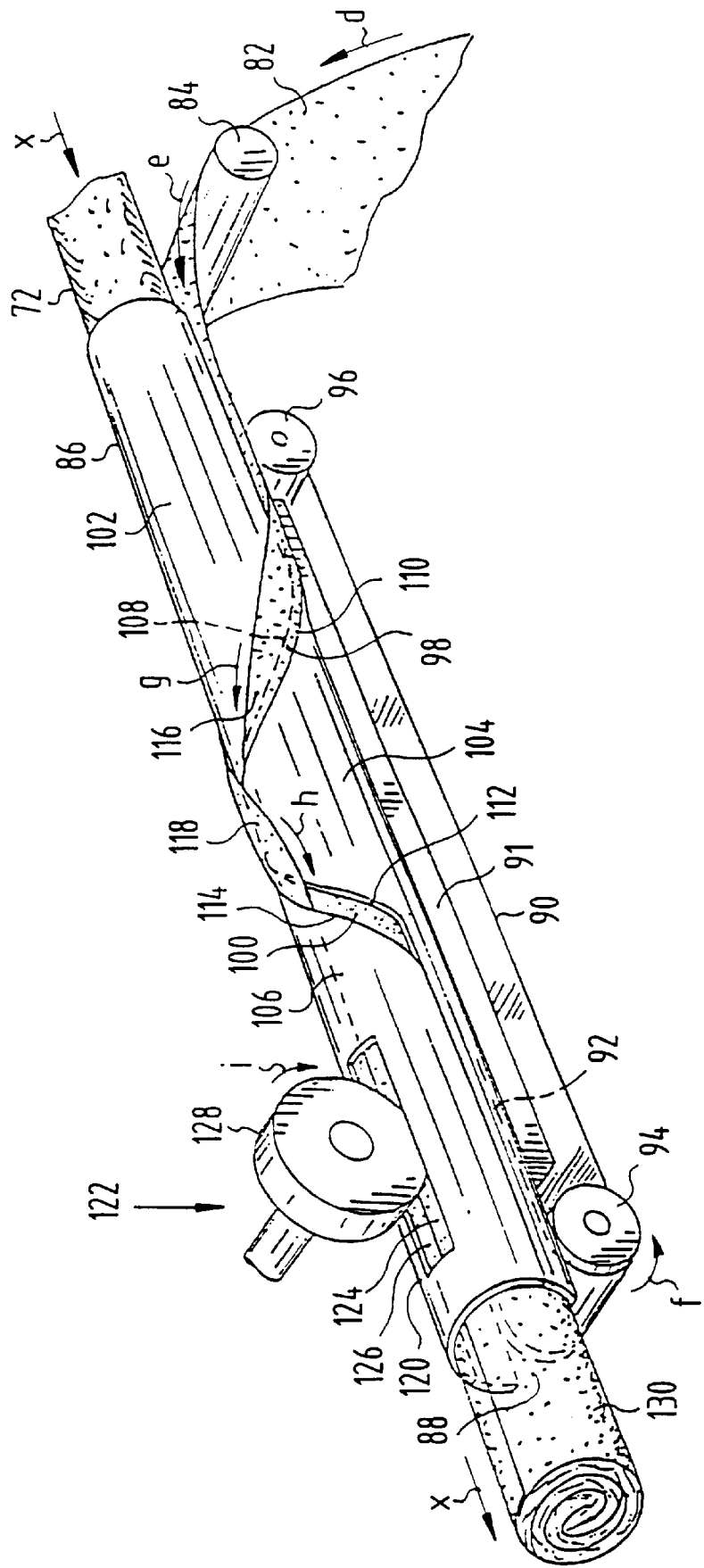
FIG. 7 shows a perspective front view of the wrapping-band attachment station.

The guide tube 86 is provided on the underside with a longitudinal slot 88 which can be seen in FIG. 7. Arranged on the underside of the guide tube 86 is an endless conveyor belt 90 which is made narrower than the longitudinal slot 88. It is thereby possible to guide an upper side 92 of the conveyor belt 90 in the region of the longitudinal slot 88 of the guide tube 86 by means of a support plate 91, in such a way that the nonwoven web 72 is taken up by frictional connection. The endless conveyor belt 90 is guided in the usual way around a driving roller 94 and a deflecting roller 96 and is driven in the direction of an arrow f, so that the upper side 92 can be driven in the direction of movement x of the nonwoven web 72 at a speed which corresponds to the conveying speed of the nonwoven web 72.

The wrapping band 82 is guided by means of the guide roller 84 between the top face of the upper side 92 of the conveyor belt 90 and the underside of the nonwoven web 72 in the region of the longitudinal slot 88 and is taken up by means of the frictional connection thereby occurring between the upper side 92 and nonwoven web 72.

The guide tube 86 is provided, on the sides on the left and right in the direction of movement x of the nonwoven web 72, with respective introduction slots 98, 100 which are formed by successively arranged segments 102, 104 and 106 of the guide tube 86. It is evident that the two introduction slots 98, 100 are offset in the axial direction of the guide tube 86. At the same time, the segment 104 is of a shape twisted in such a way that a rear edge 108 of the first segment 102, the said rear edge 108 forming an acute angle to the core of the guide tube 86 and extending in a similar way to a helix, assumes a shorter radial distance from the tube core than a front edge 110 of the segment 104, the said front edge 110 likewise limiting the introduction slot 98.

In a similar way, the radius of an edge 112 of the segment 104 at the rear in the direction of movement x is made smaller than the radius of a front edge 114 of the rear segment 106 of the guide tube 86, the said front edge 114 likewise limiting the right-hand introduction slot 100.

For reasons of clarity in the drawing, FIG. 7 does not show the wrapping band 82 in its complete width which ensures that the wrapping band has left-hand and right-hand side tabs 116, 118 which are folded upwards round the guide tube 86 by guide rollers, known per se and therefore not shown, and which slide along on the said guide tube 86. However, FIG. 7 shows the left-hand side tab 116 of the wrapping band 82, such as it is introduced into the left-hand introduction slot 98 in the direction of an arrow g beyond the outer surface of the segment 102 and is laid by means of the segment 104 onto the rounded, essentially cylindrical surface of the nonwoven web 72. In a similar way, the right-hand side tab 118 of the wrapping band 82 is subsequently likewise laid onto the surface of the rounded nonwoven web 72 by means of the segment 106 in the direction of an arrow h via the outside of the segment 104 through the right-hand introduction slot 100. At the same time, an outer longitudinal edge 124 of the right-hand side tab 118 overlaps a longitudinal edge 126 of the left-hand side tab 116 of the wrapping band 82, the said longitudinal edge 126 being laid first onto the top side of the nonwoven web 72.

FIG. 7 shows, furthermore, that the guide tube 86 is likewise provided on the top side, in the region of the rear segment 106, with a middle longitudinal slot 120 for a closing device 122 which serves for connecting the longitudinal edges 124, 126 of the side tabs 116, 118 of the wrapping band 82 to one another. In the present exemplary embodiment, the closing device 122 consists of a heat-sealing roller 128 which is made narrower than the longitudinal slot 120 and which consequently bears through the longitudinal slot on the overlapping edges 124, 126 and seals these to one another as a result of the softening of thermoplastic constituents of the wrapping band 82. The heat-sealing roller 128 can be heated in a way known per se by electrical resistance heating and can be driven in the direction of rotation of an arrow i at the conveying speed of a rounded wrapped nonwoven web 140 which leaves the guide tube 86 at the end of the latter.

Pressing Station

Figure 8:
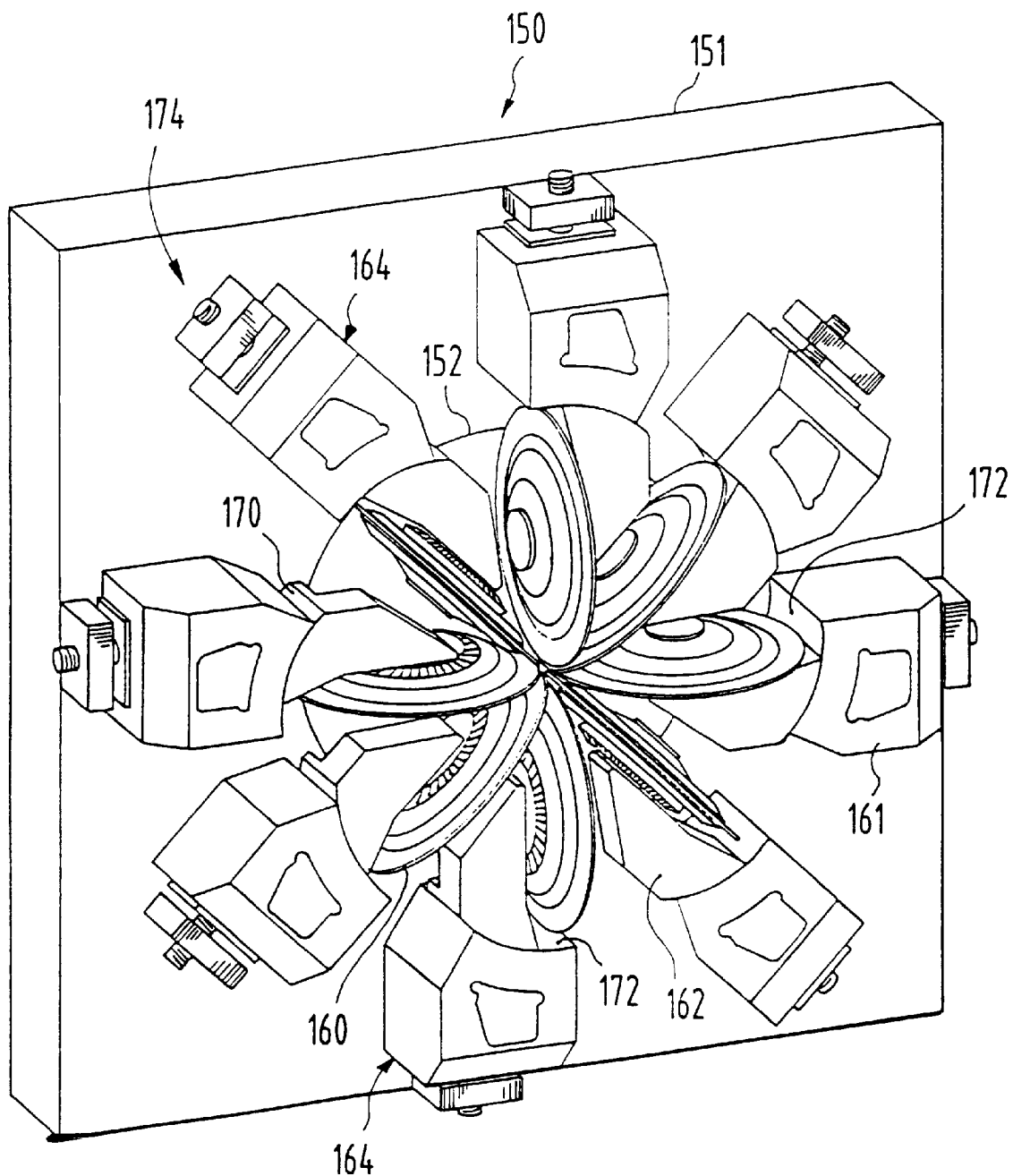
FIG. 8 shows a diagrammatic view of the exit side of a disk press according to the invention.
Figure 9:
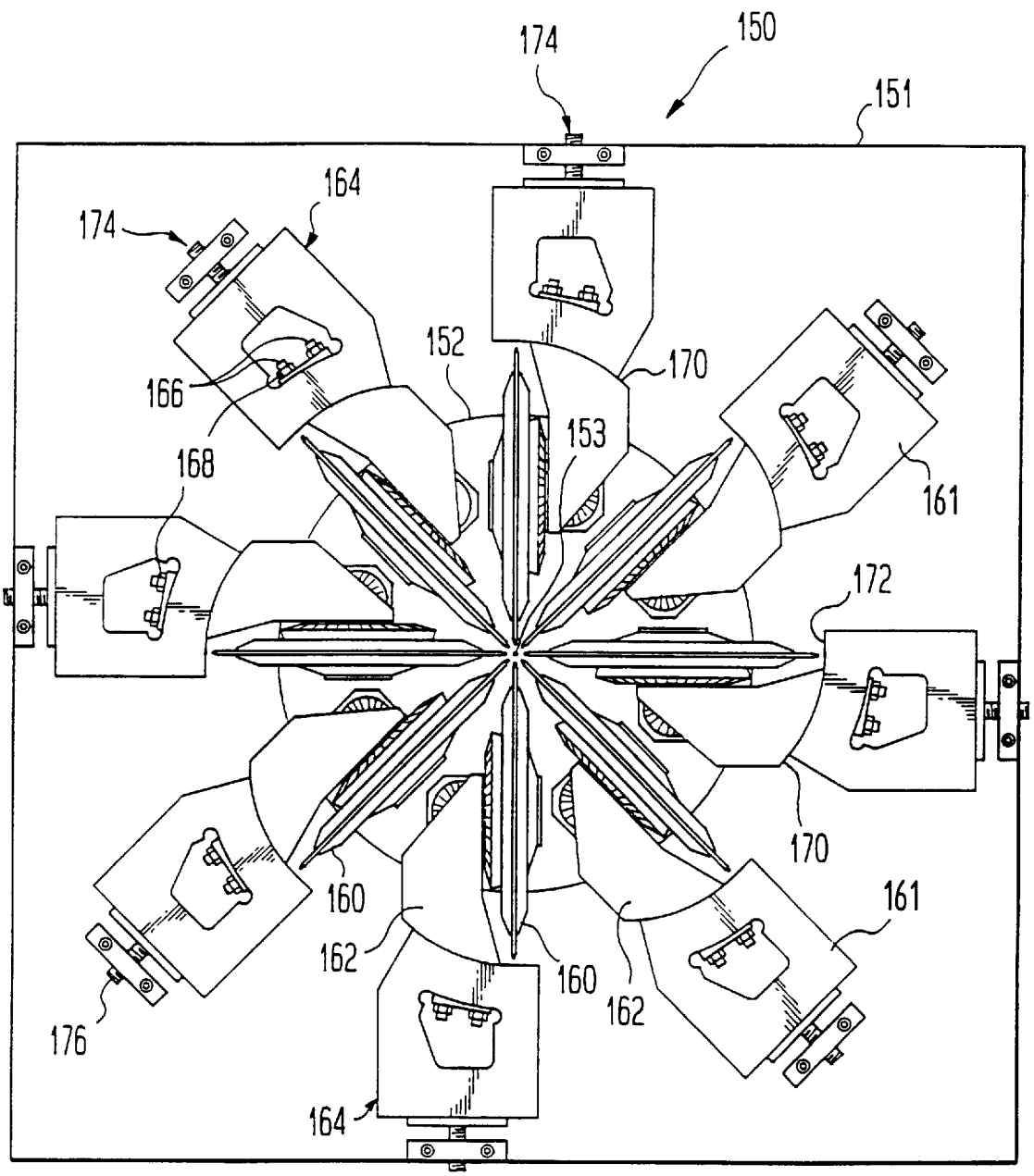
FIG. 9 shows a view of the exit side of the disk press.

FIGS. 8 and 9 show a perspective view and an orthogonal view of the exit side of a disk press 150 according to the invention. This disk press 150 consists of a vertically arranged carrier plate 151, on the exit side of which eight press disks 160 are arranged at equal circumferential angular spacings about a middle passage orifice 152 of the carrier plate 151 or a press axis 153 (FIG. 9). To produce absorption bodies for tampons of normal dimensions for feminine hygiene with a final diameter of approximately 13 mm, said eight press disks 160 having a diameter of at least 280 mm, preferably 300 mm, proved the best possible. In principle, at least three press disks 160 are required, so that a nonwoven strand can be pressed continuously to its final dimension in a single operation. However, the number of press disks and their dimension depend primarily on the composition and dimensions of the nonwoven strand to be pressed and on the desired extent of its pressing as well as on the intended use of the absorption bodies. The number of press disks 160 can therefore also be larger or smaller than eight and also be even or odd. As a rule of thumb, it may be considered that, the smaller the cross-section of the nonwoven strand and of the pressed strand obtained from this by pressing, the fewer press disks should be used, although this rule allows or necessitates modifications, depending on the form of the press disks and on the depth of their feed setting during the pressing.

The press disks 160 are fastened rotatably to respective press-disk holders 164 which are mounted on the carrier plate 151 so as to be radially adjustable relative to the passage orifice 152 of the carrier plate 151 or to the press axis 153. The press-disk holders 164 are respectively provided at their radially inner end with supporting arms 162, on the radially inner end of each of which one of the essentially circular press disks 160 is mounted so as to be drivable about its axis 190 in the direction of rotation. All eight press-disk holders 164 are positioned, together with their supporting arms 162 and the press disks 160, on the carrier plate 151 in a plane which is directed perpendicularly to the core of the passage orifice 152 or to the press axis 153. Furthermore, all the press disks 160 can be driven synchronously with the effect of a simultaneous conveyance and pressing of the nonwoven strand, as explained in more detail further below.

The supporting arms 162 are respectively fastened axially adjustably on the press-disk holders 164, so that a fine adjustment to each press disk 160 radially to the press axis 153 is possible. Moreover, according to FIGS. 13 and 14 the supporting arms 162 are adjustable on bearing blocks 161 of the press-disk holders 164 about an axis parallel to the press axis 153, in such a way that the press disks 160 can be adjusted parallel to themselves out of their plane radial to the press axis 153, but also into another angular position relative to the radial plane (inclination). This adjustability of the supporting arms 162 and of the press disks 160 connected to them makes it possible, during pressing, to control or adjust the important straight run-out and the rectilinear profiling of the pressed strand during the pressing of the latter.

Figure 10:
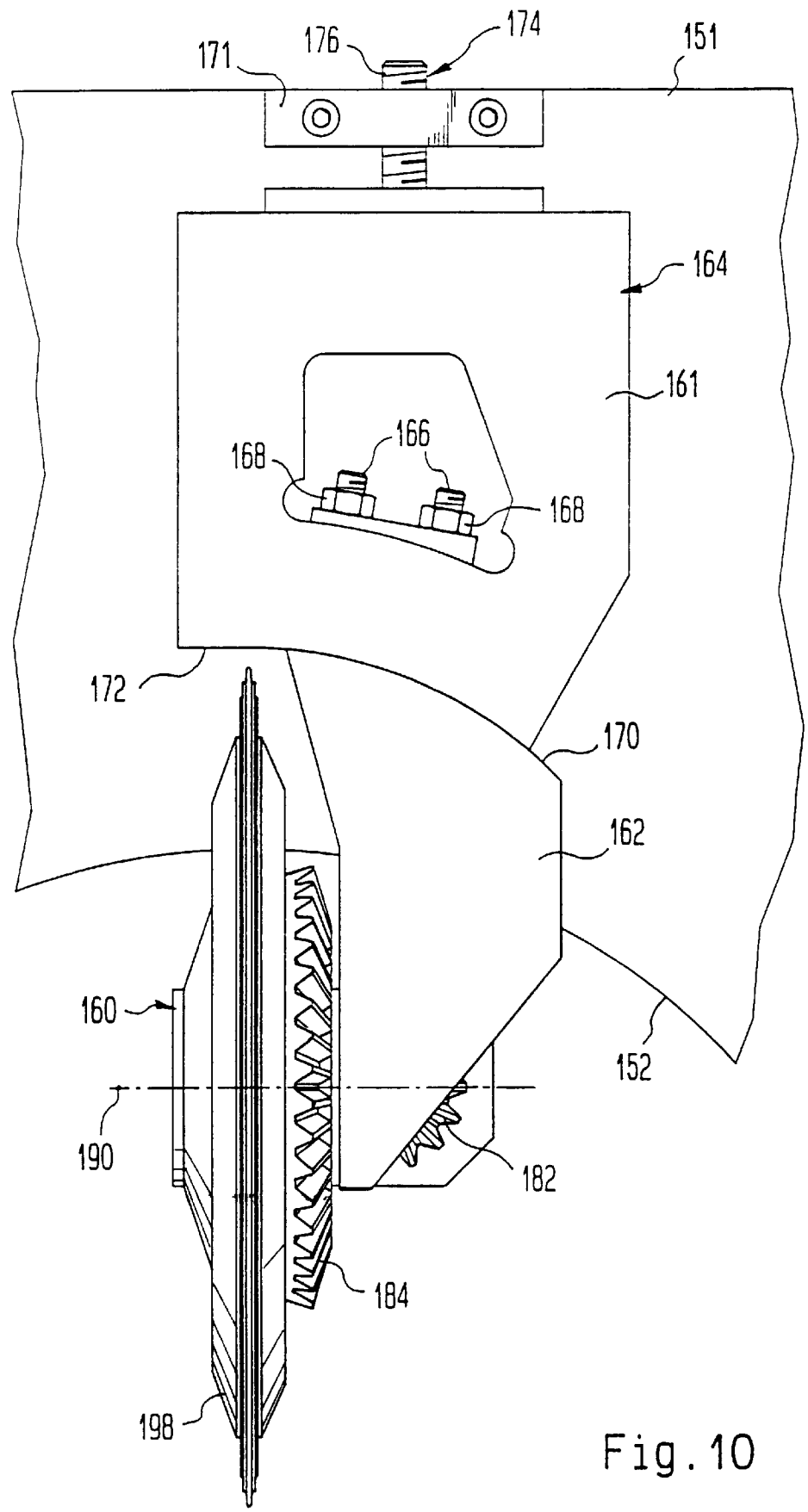
FIG. 10 shows a cutout from the disk press shown in FIG. 8, with a press-disk holder and with a press disk fastened rotatably to it.

In particular, it is evident from FIGS. 9 and 10 that each press-disk holder 164 is provided with screw bolts 166, by means of which the associated supporting arm 162 can be fixed in a desired angular position by means of screw nuts 168.

According to FIGS. 8, 9 and 10 each supporting arm 162 bears with a guide face 170 in the form of a cylinder cutout against a correspondingly shaped stop face 172 of the press-disk holder 164. The centre of curvature of the said faces 170, 172 is located in the middle of the press disk 160.

Furthermore, FIGS. 8, 9 and 10 reveal an actuating device 174 for the press-disk holder 164, by means of which each press-disk holder 164 is radially adjustable individually. In the present case, the actuating device 174 comprises eight holding plates 171 (FIG. 10) which are fastened on the rear side of the carrier plate 151 perpendicularly to the press axis at equal angular spacings and in which actuating bolts 176 are mounted rotatably, but non-adjustably axially. These actuating bolts 176 are each connected to a press-disk holder 164 by means of a screw thread not shown, so that, as a result of the rotation of the actuating bolts 176, each press-disk holder 164 can be moved to and fro and therefore the radial distance of the press disk 160 from the press axis and consequently the depth of penetration of the press disks 160 into the nonwoven material can be set exactly.

Figure 11:
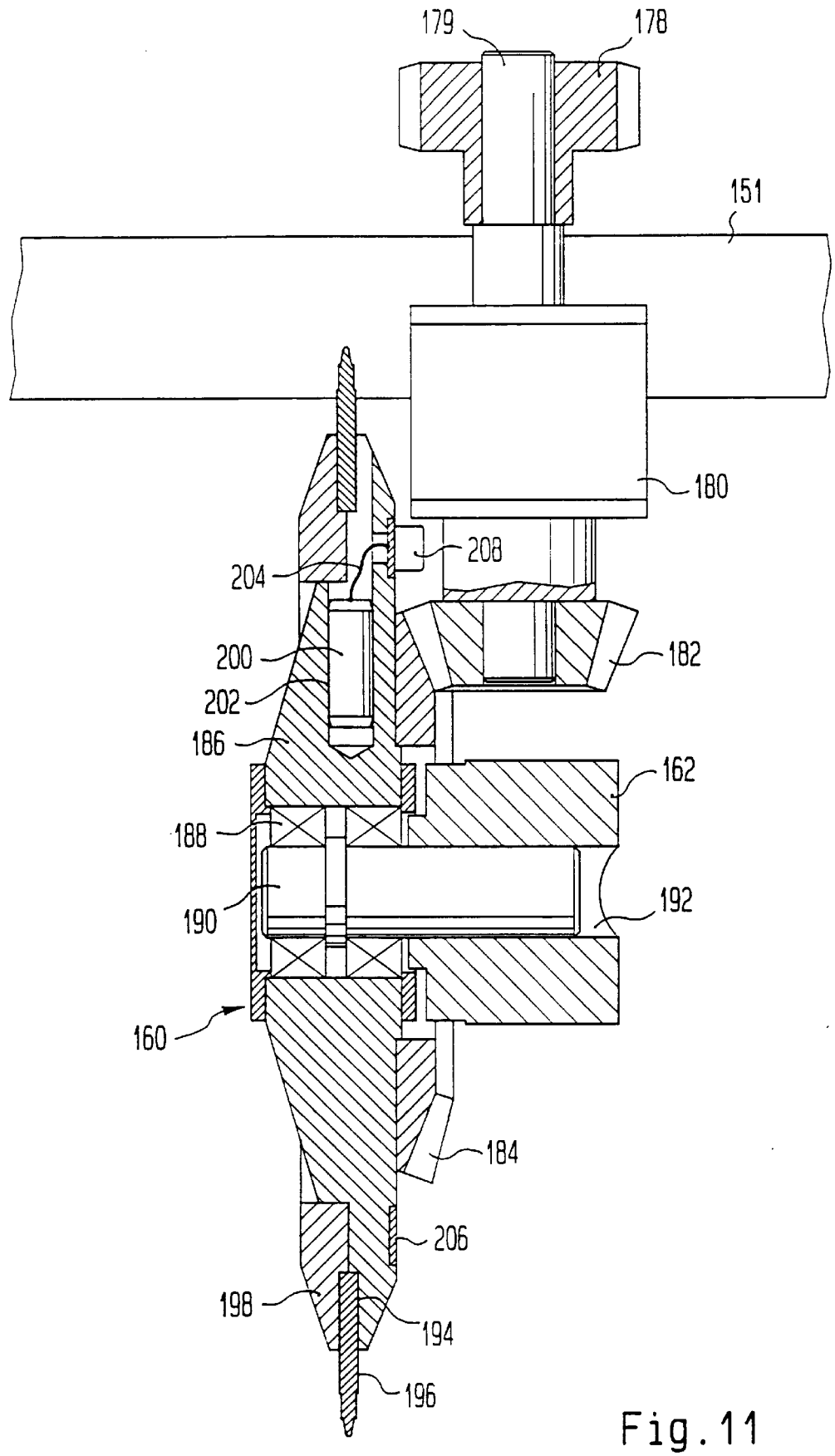
FIG. 11 shows a middle longitudinal section through a press disk and a bevel-wheel drive.

The drive of each press disk 160 can be seen in more detail from FIGS. 10 and 11. According to FIG. 11, a spur wheel 178 is fastened on a transmission shaft 179 which is rotatably mounted axis-parallel to the press disk 160 in a bearing 180 and which is provided at its radially inner end with a driving bevel wheel 182. This driving bevel wheel 182 meshes with a bevel-wheel disk 184 which is fastened to one end face of a press-disk body 186 by means of screws not shown. The press-disk body 186 is mounted rotatably by means of a roller bearing 188 on the axis 190 which is axially adjustable in a bore 192 of the supporting arm 162.

The press-disk body 186 is provided, on its outer end face facing away from the supporting arm 162, with an outer stepped annular face 194 for receiving a press-ring disk 196 which can be clamped firmly against the annular face 194 of the press-disk body 186 by means of a correspondingly shaped clamping ring 198. This construction allows an economical use of valuable materials for the overall construction of the press disks 160 and a rapid exchange of their press-ring disks 196.

In each press-disk body 186, electrical resistance-heating elements 200 are arranged at equal circumferential angular spacings in radial bores 202 of the press-disk bodies 186 and are connected via an electrical line 204 to a slip ring 206 which is located on the inner end face of the press-disk body 186 and against which a stationary wiper contact 208 bears. A heating of the press disks 160 by means of the resistance-heating elements 200 can be desirable, for example when only natural-fibre material is to be subjected to a pressing operation. In contrast, a heating of the press disks 160 can, as a rule, be forgone or even be inexpedient if the fibre material to be pressed contains fibres which consist completely or partially of thermoplastic material.

Figure 12:
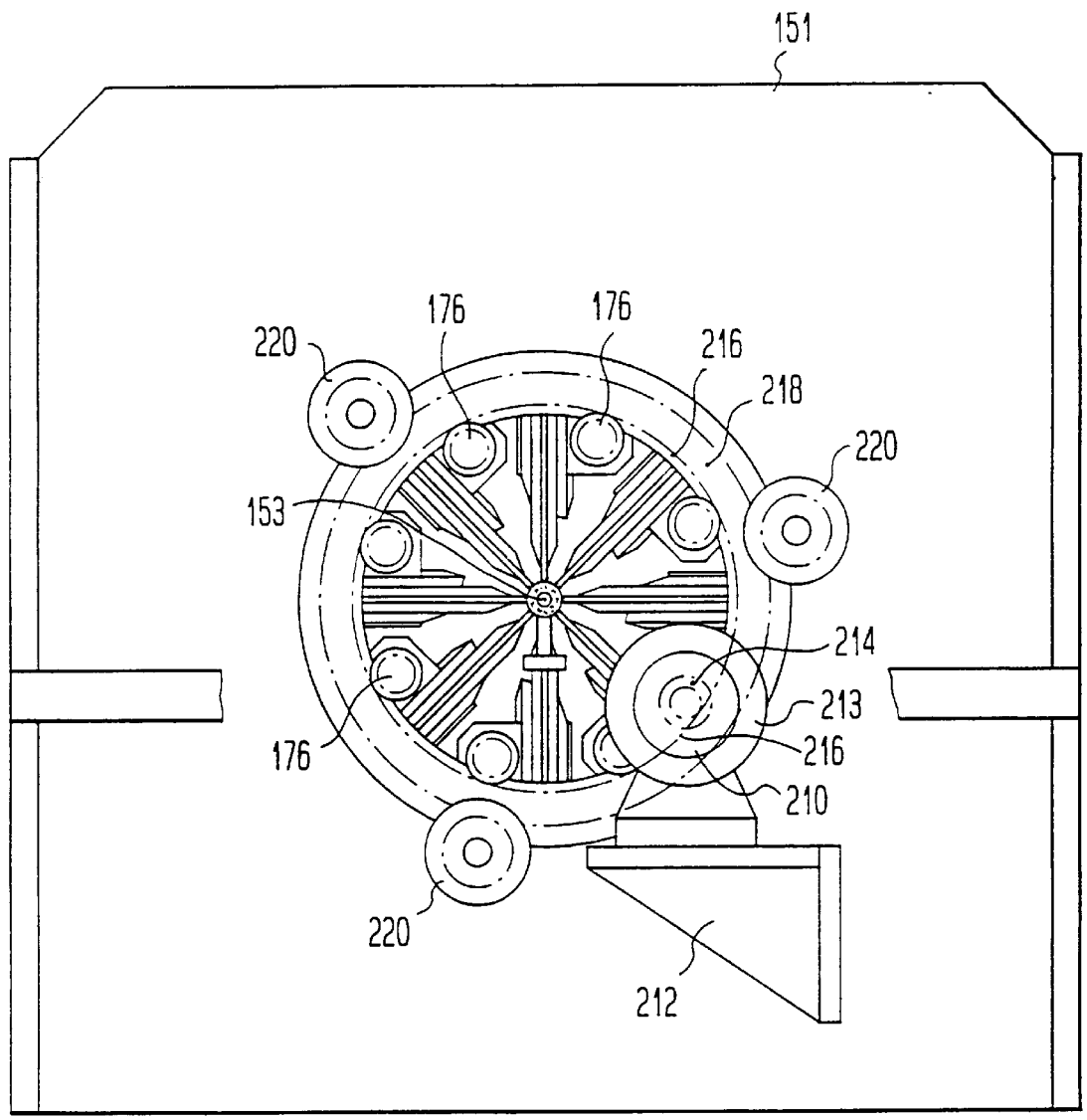
FIG. 12 shows a view of the entry side of the disk press, with a drive motor for a toothed ring synchronously driving the press disks.

A drive motor 210, which is supported on a bracket 212 fastened to the carrier plate 151, can be seen from the view of the entry side of the carrier plate 151 in FIG. 12. Connected to the drive motor 210 via a reduction gear 213 is a driving spur wheel 214 which cooperates with an internal toothing 216 of a toothed ring 218. The toothed ring 218 is rotatably mounted concentrically to the press axis 153 on the carrier plate 151, parallel to the main plane of the latter, on three bearing rollers 220 which are fastened freely rotatably to the carrier plate 151 at equal angular spacings relative to and at equal radial distances from the press axis 153. The internal toothing 216 of the toothed ring 218 meshes respectively with the spur wheel 178, shown in FIG. 11, of each press-disk holder 164, so that each press disk 160 can be driven synchronously by the toothed ring 218 by means of the drive motor 210. This ensures that the nonwoven strand to be pressed is uniformly and exactly conveyed coaxially relative to the press axis 153.

Figure 13:
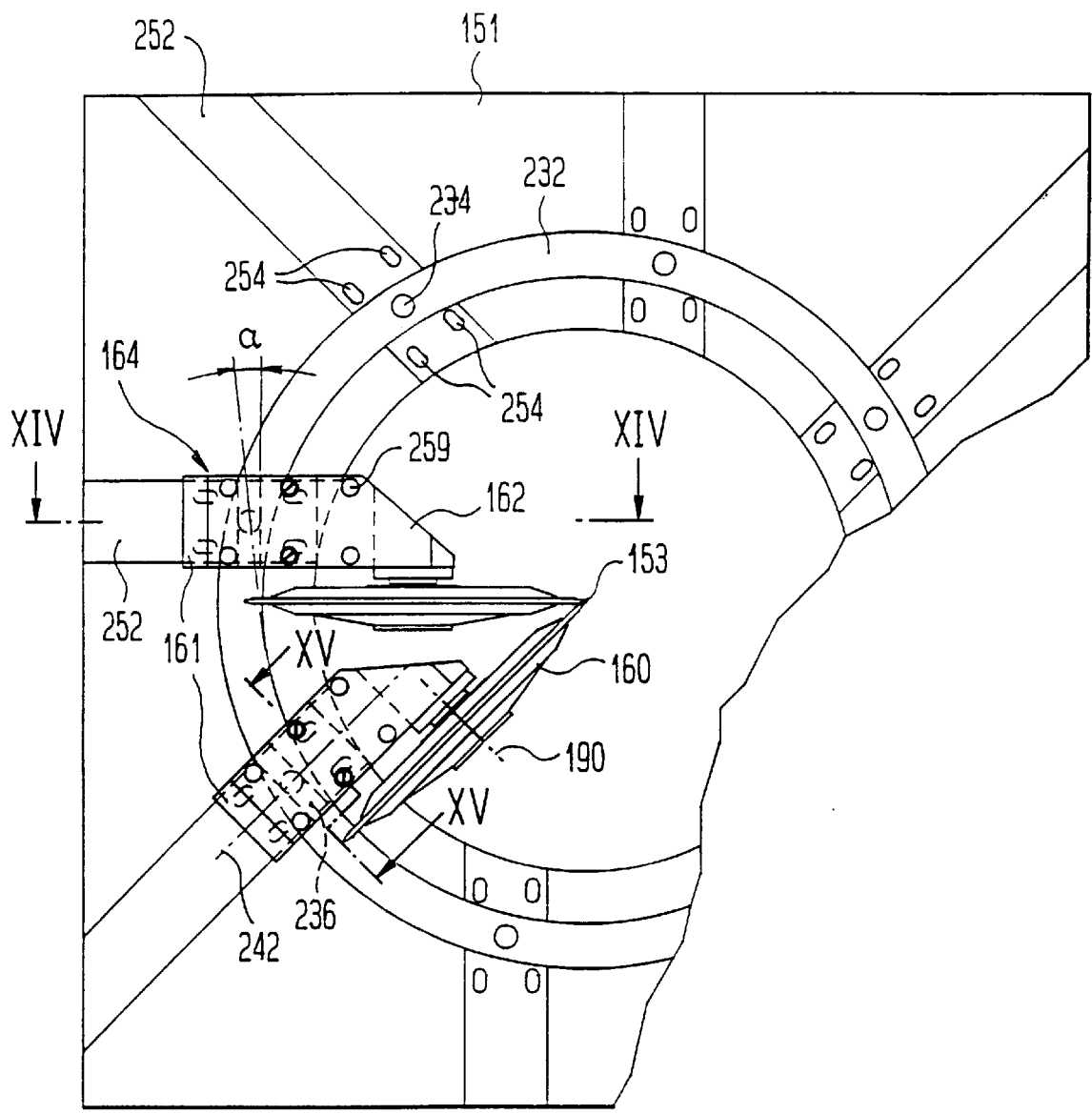
FIG. 13 shows a partially cutaway view of a device for the simultaneous adjustment of the press-disk holders by means of a rotatable control ring.
Figure 14:
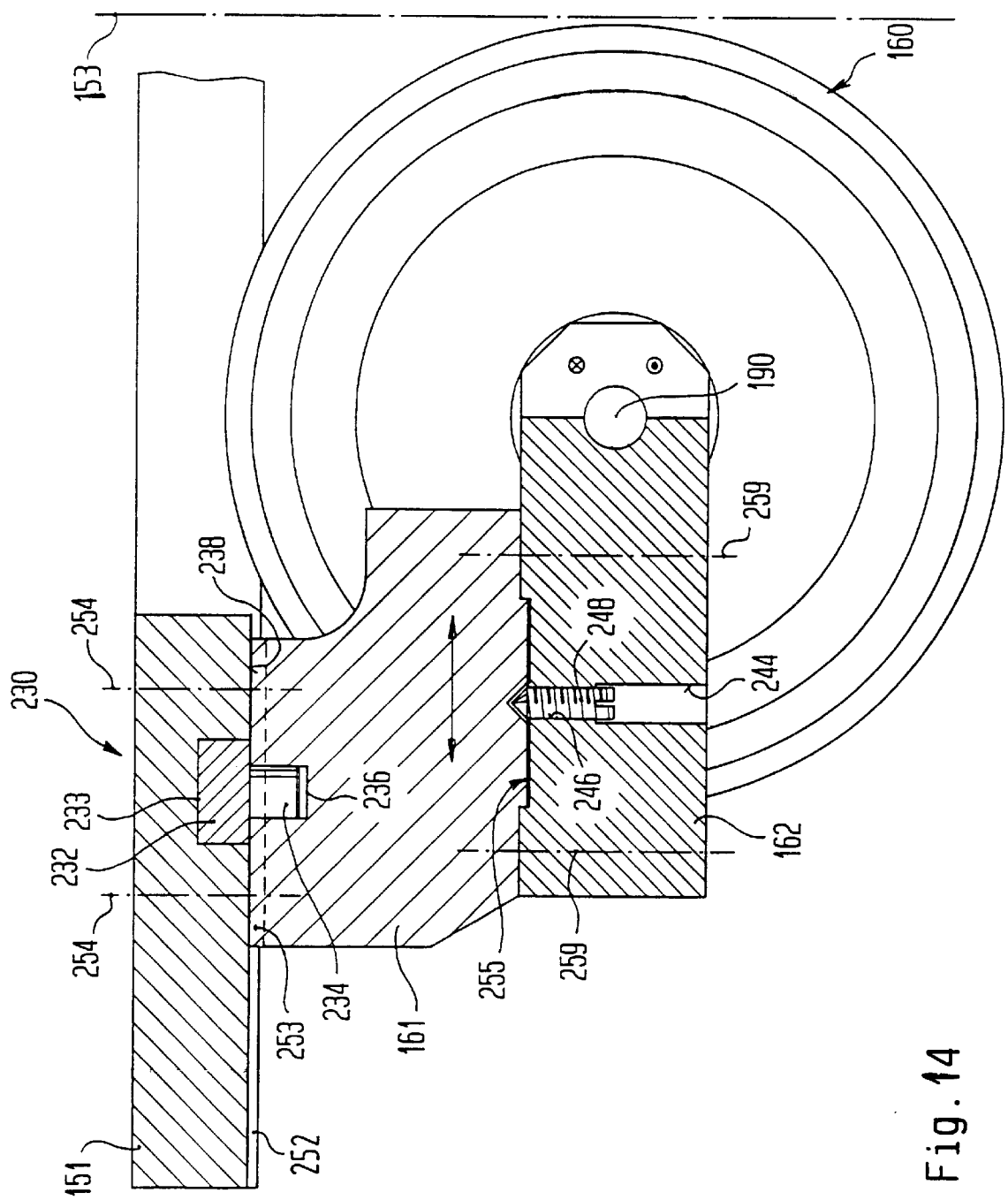
FIG. 14 shows a sectional view along the line 14—14 in FIG. 13.
Figure 15:
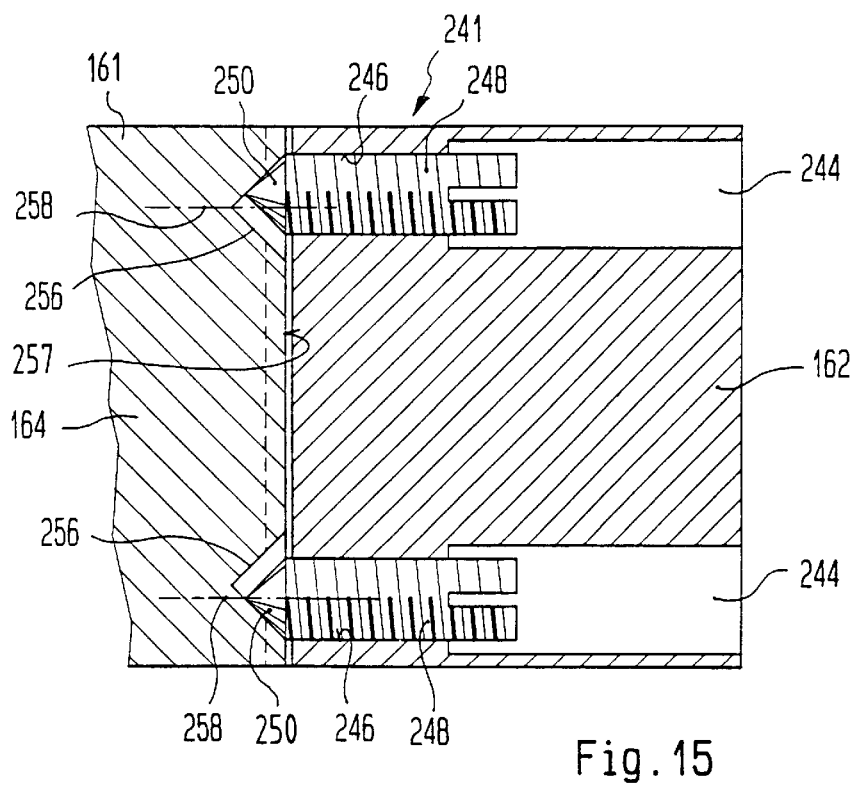
FIG. 15 shows a sectional view along the line 15—15 in FIG. 13.

FIGS. 13, 14 and 15 show a device, by means of which the press-disk holders 164 are synchronously adjustable radially to the press axis 153. For this purpose, the carrier plate 151 has, on its entry side, eight guides 252 which are parallel to the radial press-disk planes and which are arranged at a distance from and parallel to the radial planes of the press disks 160 in FIG. 13. The bearing blocks 161 of the press-disk holders 164 engage by means of guide tongues 253 into these guides 252 in the manner of a tongue-and-groove connection. In the bottom of each guide 252, four long holes 254 limiting a rectangle are arranged in pairs symmetrically and parallel to a longitudinal mid-axis 242 of each guide 252 as well as parallel to the axis 190 of the associated press disk 160 (FIGS. 13 and 14). Fastened to the underside of the guide tongue 253 of each bearing block 161 are screw bolts, not shown, which engage into the said long holes 254 and which fix the bearing block 161 of each press-disk holder 164 to the carrier plate 151 by means of screw nuts or allow a radial adjustment of the press-disk holders 164 to the extent limited by the long holes 254, as can be taken from FIGS. 13 and 14.

A device 230 for the synchronous radial adjustment of the press-disk holders 164 for the press disks 160 is illustrated in FIG. 14. This adjustment device 230 consists of a control ring 232 which is rotatably mounted concentrically to the press axis 153 in a circular groove 233 on the entry side of the carrier plate 151 in a plane parallel to the main plane of the latter. Furthermore, the control ring 232 is provided, on its front side facing away from the carrier plate 151, with a number of control bolts 234 corresponding to the number of press-disk holders 164 (FIGS. 13 and 14), the said control bolts 234 of course, once again, being fastened to the control ring 232 at equal circumferential angular spacings and projecting outwards perpendicularly to the main plane of the latter. These control bolts 234 each engage into a control groove 236 which is arranged, in a direction perpendicular to the longitudinal direction and direction of adjustment of each press-disk holder 164, in a supporting face 238 of the bearing block 161 of each press-disk holder 164, the said supporting face 238 facing the control ring 232. It is evident from FIG. 13 that the control grooves 236 in bearing blocks 161 of each press-disk holder 164 consequently form, with a tangent drawn to the control ring 232 along a longitudinal mid-axis of the control bolt 234, an acute angle which ensures that the press-disk holders 164 can be synchronously adjusted radially inwards in the event of a rotation of the control ring 232 in the clockwise direction and correspondingly radially outwards in the event of a rotation in the anti-clockwise direction. An extremely accurate synchronous feed setting of the press disks 160 and adaptation of these to the particular nonwoven strand to be pressed, in particular to its fibre-material density and diameter, are thereby possible.

Furthermore, FIG. 15 shows an arrangement 241 of particular importance for a precision adjustment of the supporting arms 162 in the direction of the axis 190 of each of the press disks 160 as shown in FIGS. 13, 14 and 15. This arrangement 241 consists of two countersunk bores 244 in the supporting arm 162 of each of the press-disk holders 164 (FIG. 15), which are arranged symmetrically to the longitudinal mid-axis 242 of the guide 252 and which open out into threaded bores 246, into which adjusting screws 248 are screwed. The adjusting screws 248 are provided with cone tips 250 at their front end.

According to FIGS. 13, 14 and 15, the supporting arm 162 is mounted adjustably parallel to the axis 190 of the press disk 160, on the outside of the bearing block 161 facing away from the carrier plate 151, by means of a tongue-and-groove guide 255 and is fastened releasably by means of four screw connections 259 merely indicated by dot-and-dash lines in FIGS. 13 and 14. For this purpose, there are provided in a supporting face 257 of the bearing blocks 161 for the supporting arms 162 transverse grooves 256 of small length which have a V-shaped cross-section and which are arranged at a distance from and parallel to one another in a plane perpendicular to the longitudinal mid-axis 242 of the guides 252. According to FIG. 15, longitudinal mid-axes 258 coinciding with the vertex point of the V-profile of the transverse grooves 256 are offset laterally inwards relative to the cone tips 250 of each pair of adjusting screws 248. Since the cone angle of each cone tip 250 of the adjusting screws 248 corresponds to the angle of the V-shape transverse profile of the transverse grooves 256, the cone tip 250 of the adjusting screws 248 therefore bears respectively against one of the two groove walls of the transverse grooves 256 facing away from one another. It is therefore understandable that, depending on the screw-in depth of the adjusting screws 248 into the transverse grooves 256, each press-disk holder 164, together with the press disk 160 fastened to it, can be adjusted extremely finely parallel to the axis 190 of the press disk 160 in the direction of the tongue-and-groove guide 255. This adjustability of the press disks 160 parallel to themselves out of their plane radial to the press axis 153 makes it possible, depending on the type of material used, for the nonwoven strand to be pressed and on the depth of penetration of the press disks 160 into the nonwoven strand, to achieve an exact straight run-out of the press strand during and after the pressing of the longitudinal grooves 131 into the fibre material.

In FIG. 15, the countersunk bore 244, together with the adjusting screw 248 and the V-shaped transverse groove 256, is shown shifted into the sectional plane, from which it is evident that the adjusting screws 248 engage free of play into the transverse grooves in the direction of the tongue-and-groove guide 255.

Figure 16:
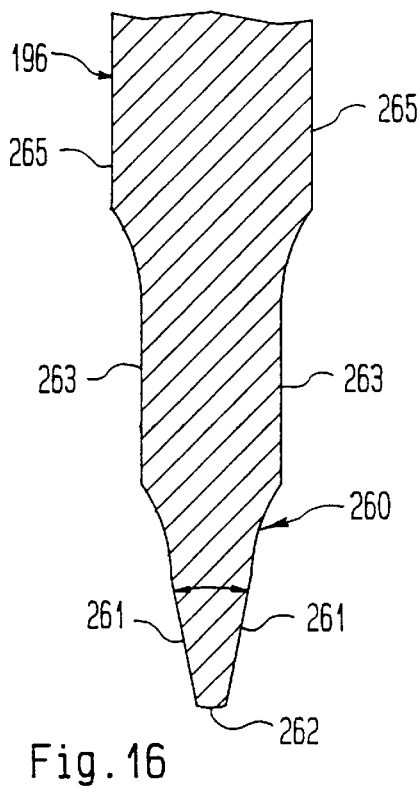
FIGS. 16 and 17 show two different press-disk transverse profiles.

FIG. 16 shows a transverse profile 260 of a press-ring disk 196 made of steel, the diameter of which is expediently in the range of 280 to 300 mm for the pressing of absorption bodies, especially for feminine hygiene, and the outer, rounded pressing edge 262 of which has a width of approximately 0.723 mm. A transverse profile 260 widens radially inwards in a V-shaped manner, profile flanks 261 forming an acute angle of 22.5° and merging into parallel side faces 263 at a radial distance of 5.543 mm from the pressing edge 262. These parallel side faces 263 run out, at a radial distance of 12.332 mm from the pressing edge 262, into parallel end faces 265, between which the press-ring disks 196 are 5.0 mm wide. This profile of the press-ring disk 196 proves appropriate particularly in respect of a fibre material which has a smooth surface and which therefore generates relatively little friction relative to the press-ring disk 196 during the pressing.

Figure 17:
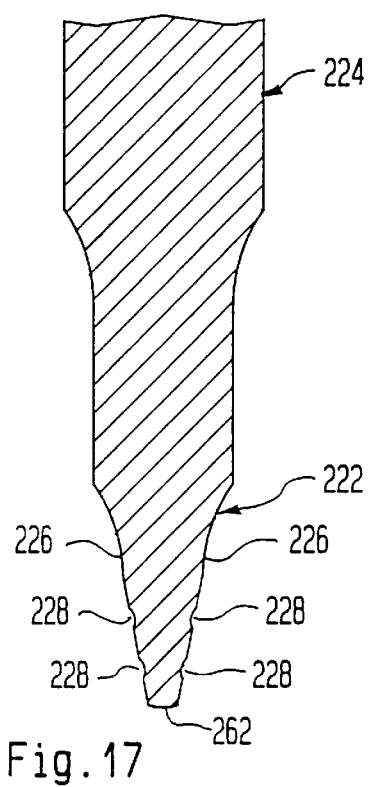

For materials which have a less smooth surface or which are to be carried to the core of the press strand to a lesser extent during the pressing, under some circumstances it can be advantageous to have a transverse profile 222, shown in FIG. 17, of a press-ring disk 224, in which, as can be seen, profile flanks 226 possess, in contrast to the transverse profile 260 shown in FIG. 16, annular grooves 228 of arcuate cross-section which are arranged at a distance from one another concentrically to the mid-axis of the press-ring disk 224 and which generate reduced friction and consequently reduced heating relative to the material of the strand to be pressed and therefore also compact the material to be pressed to a lesser extent in the direction of the longitudinal mid-axis of the nonwoven strand. If appropriate, the angle-forming profile flanks of the transverse profile of the press-ring disks can also be roughened by knurling, knobs, projecting annular beads or an enamelling, depending on the material of which the strand to be pressed is composed and which compaction and conveying speed of the material during the pressing are desired.

Figure 18:
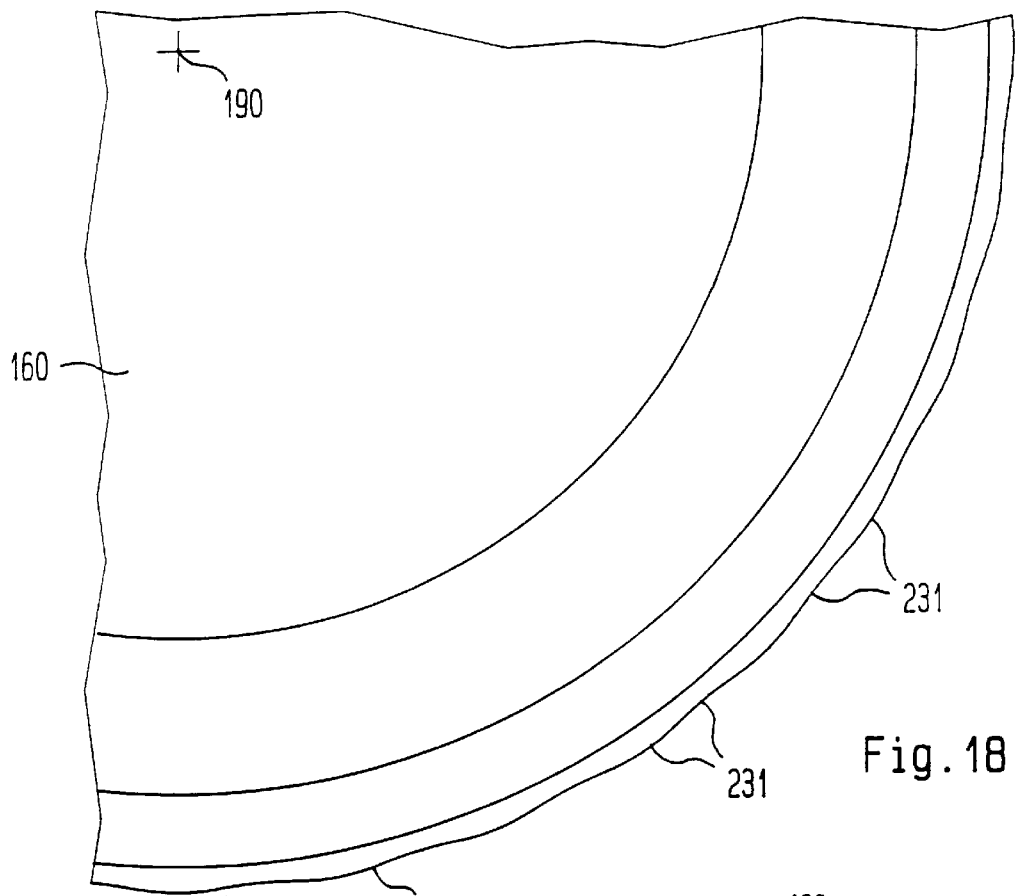
FIG. 18 shows a view of a partially cutaway press disk having a corrugated circumferential profile.

Since the press disks 160 are all driven, in order to convey the nonwoven strand simultaneously, during the pressing, towards the exit side of the disk press 150, to one of the downstream machining stations, it can be desirable to provide one or more or all press disks 160 with an irregular pressing edge. Thus, FIG. 18 shows a pressing edge 229 of a press-ring disk 227 which has corrugations 231 in the circumferential direction. This corrugated pressing edge 229 allows a varying compaction of the fibre material in the core of a pressed strand 240 and, at the same time, can assist the conveyance of the pressed strand.

Depending on the fibre material used for the strand to be pressed, the pressed edge can, if appropriate, also have a type of toothing and/or knurling, in contrast to the exemplary embodiment shown in FIG. 18. The foregoing statements illustrate the importance of the surface nature and thickness of the press-ring disks, a particular roughness or depth of roughness of, for example, 8–10 microns proving advantageous, so that the task of simultaneous conveyance and pressing of the nonwoven strand can be mastered. Furthermore, it is necessary to ensure a high bending resistance of the press-disk bodies and of the press-ring disks clamped in them, with regard to the considerable forces to which they are exposed during the pressing and conveyance of the nonwoven strand.

Figure 20:
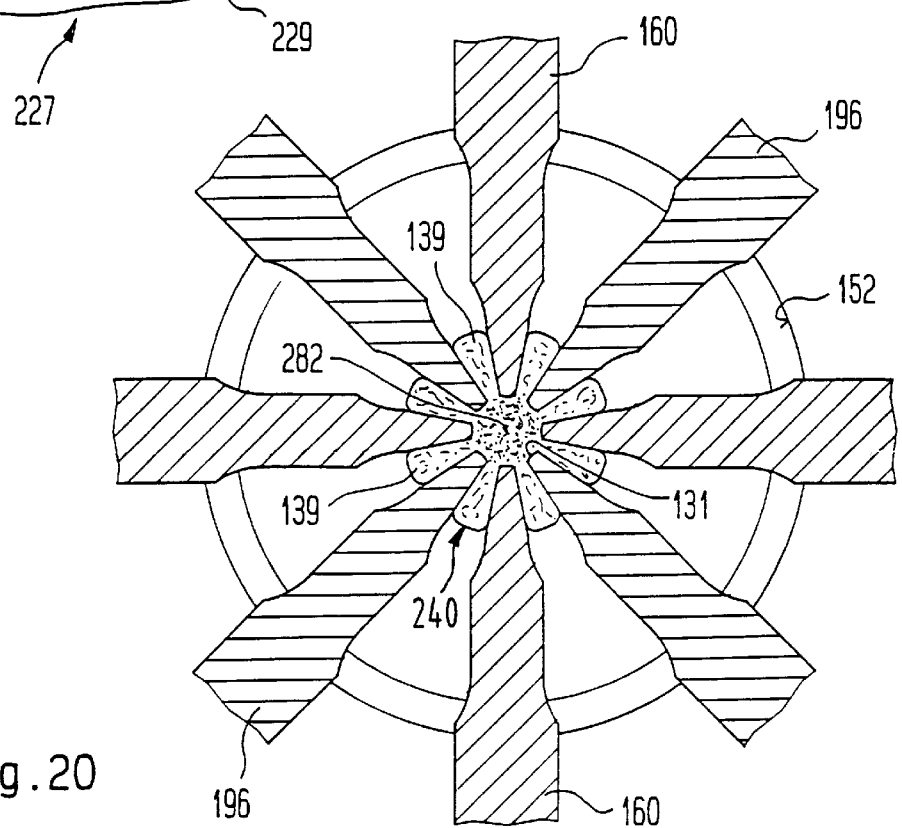
FIG. 20 shows a cross-section of the disk-press gap with a press strand compressed by eight press disks.
Figure 19:
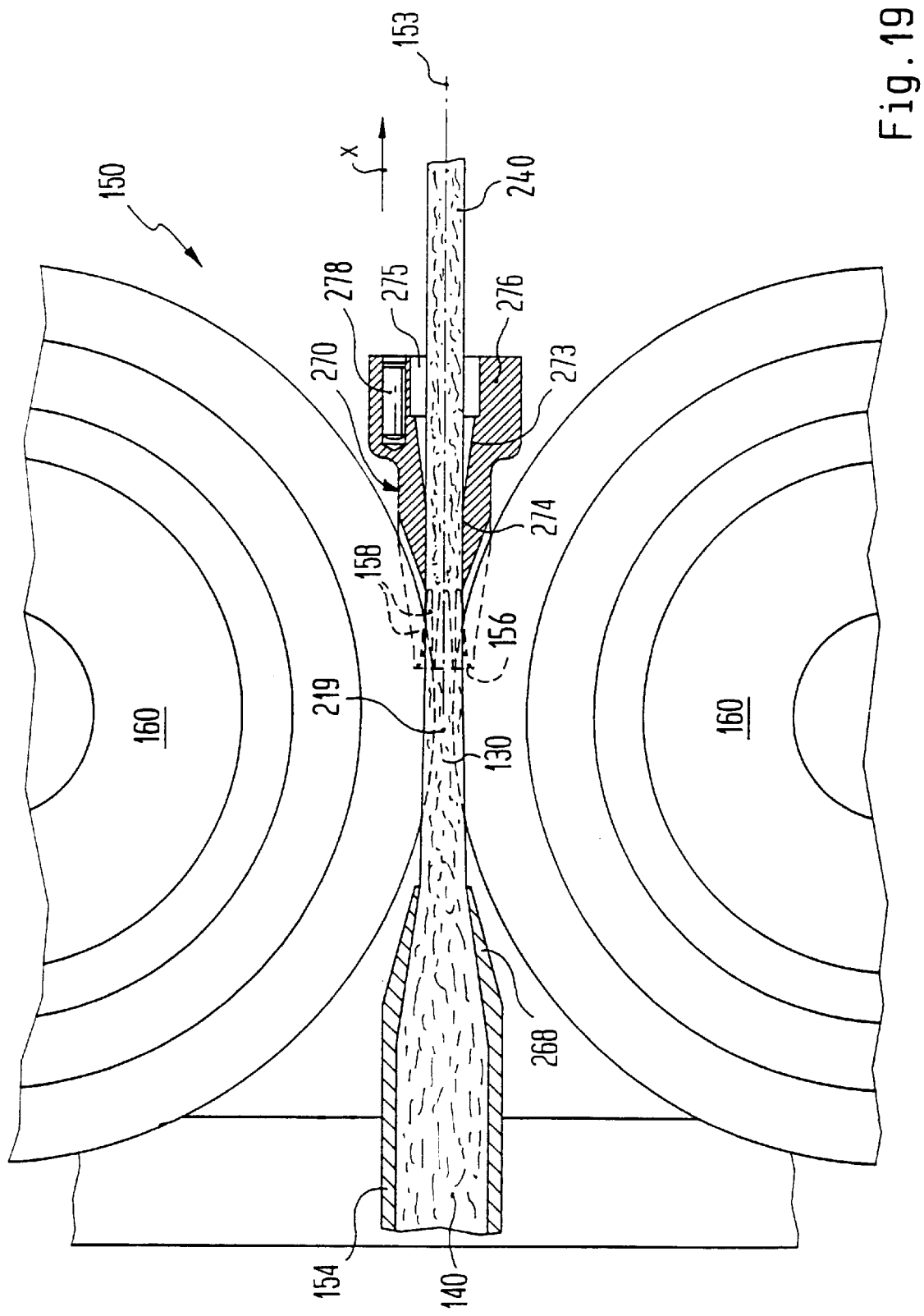
FIG. 19 shows a view of two press disks located opposite one another in a diametral plane and having a supply nozzle and a catch nozzle, in longitudinal section.

FIG. 19 shows, on the entry side of the disk press 150, a tubular piece 154, the free cross-section of which is narrowed in the form of a supply nozzle 268 at the front end. As regards the production of absorption bodies of normal size for feminine hygiene, a reduction in cross-section of the supply nozzle 268 in relation to the cross-section of the tubular piece 154 of approximately 9% or in a ratio of 8:7 proves appropriate. This cross-sectional ratio can, of course, be varied in dependence on parameters to be taken into account. The tubular piece 154 is arranged coaxially to the press axis 153 or a press-disk gap 219 and serves for supplying the nonwoven strand 140 consisting of a compressible material, preferably natural, biologically degradable fibre material, such as cotton fibres. By means of the supply nozzle 268, the round cross-section of the nonwoven strand 140 is compressed and subsequently is guided freely into the press-disk gap 219 between the eight press disks 160 located diametrically opposite one another in pairs. In the present exemplary embodiment of the production of absorption bodies for feminine-hygiene tampons, the nonwoven strand 140 is compressed to form a pressed strand 240 having a cross-sectional diameter of 15 mm. At the same time, as shown in FIG. 20, eight longitudinal grooves 131 and eight longitudinal ribs 139 are formed. In a narrowest press-disk gap 219 shown in FIG. 19, the pressing edges of the eight press disks 160 form said pressed strand 240, the core of which has a diameter of approximately 4 mm in the present exemplary embodiment.

Furthermore, in FIG. 19, a catch nozzle 270 for the pressed strand 240 is arranged at a distance behind the narrowest press-disk gap 219 in the conveying direction x. This axial distance can, for example, be 10 to 15 mm from the press-disk gap 219. A widened entry orifice 156 of this catch nozzle 270 is dimensioned somewhat larger than the cross-section which the pressed strand 240 assumes behind the narrowest cross-section of the press-disk gap 219. Thus, the entry cross-section of the catch nozzle 270 can have a diameter of, for example, 18 mm. The catch nozzle 270 is provided with a number of longitudinal slots 158, namely eight, having the same length and width and corresponding to the number of press disks, the said longitudinal slots 158 extending at equal angular spacings over the circumference of the catch nozzle 270 in the planes of the respective associated press disk 160, and each engaging radially and with free play into one of the eight press disks 160. The longitudinal slots 158 extend, for example, over a length of 30 mm. The free cross-section of the catch nozzle 270 narrows behind the longitudinal slots 158 over a middle length portion 274 at least to the narrowest cross-section of the press-disk gap 219. This middle length portion 274 can have a length of 10 mm and a clear, circular-cylindrical cross-section with a diameter of 11 mm. That is to say, the cross-section of the pressed strand 240 is reduced appreciably in the middle length portion 274 of the catch nozzle 270 in relation to the cross-section of the pressed strand 240 in the press-disk gap 219. This reduction in cross-section of the catch nozzle 270 serves for closing the pressed-in, open longitudinal grooves 131 by an abutment of the radially outer ends of adjacent ribs 139 of the pressed strand 240 to provide a substantially cylindrical outer surface of the pressed strand 240 having longitudinal open channels inside of said closed grooves. In contrast thereto, it is also possible to provide the middle length portion 274 of the catch nozzle 270 with a clear cross-section by which the cross-section of the catch nozzle 270 serves for maintaining the pressed-in open longitudinal grooves 131 of the pressed strand 240. Thus, the final diameter of the pressed strand 240 and the characteristic and structure of its surface, f.i. also its open longitudinal grooves 131 as shown in FIG. 20, can be strongly affected by varying the inside diameter of the middle length portion 274 of a catch nozzle 270.

The catch nozzle 270 is widened over an end portion 276 in the conveying direction of the arrow x. The end portion 276 is reinforced in a flange-like manner and is provided with electrical resistance-heating elements 278, by means of which the catch nozzle 270 can be heated to an ironing temperature in the range of 70 to 90° C. for the pressed strand 240. As a result, if desired, a smoothing or ironing effect can be exerted on the surface of the pressed strand 240. This ironing effect can be employed advantageously when a nonwoven web 140 consists solely of natural or cellulose-containing fibres, that is to say contains no thermoplastic fibres or constituents. In contrast, heating may be inexpedient, for example when the nonwoven web 140 is wrapped in a non-woven material which consists at least partially of thermoplastic material, such as polyethylene or polypropylene, in order to improve the capillary action relative to the inside of the absorption body. A conical widening 273 of the clear cross-section at the exit end of the catch nozzle 270 allows some expansion of the pressed strand 240 as a result of the inherent elasticity of its fibre material. This cross-sectional widening 273 can, for example, have a clear diameter of 12 to 12.5 mm. A cylindrical end portion 275 of the cross-sectional widening 273 serves for the reception of and as a stop for a plastic tube of corresponding diameter which is not shown and which is mounted in a floating manner in the end portion.

FIG. 20 shows the press-disk gap 219 in cross-section, the eight press disks 160 each pressing into the pressed strand 240 one of the eight longitudinal grooves 131 extending in the longitudinal direction of the pressed strand, and at the same time forming a central pressed-strand core 282 of greater compaction of the material. Formed between the flanks of the adjacent press disks 160 are eight longitudinal ribs 139, in which the material is radially outwardly subjected to increasingly lower compaction. The greater capillary action achieved thereby can be utilized in an advantageous way for the absorption of fluids, depending on the intended use of the pressed strand 240 and of the articles produced from it.

If it is desired to achieve an essentially cylindrical circumferential face of the pressed strand 240, this can be attained by a greater or lesser reduction of the cross-section in the middle length portion 274, shown in FIG. 19, of the catch nozzle 270, in conjunction with the ironing effect provided there for the outer circumference of the pressed strand 240 as mentioned above.

Figure 21:
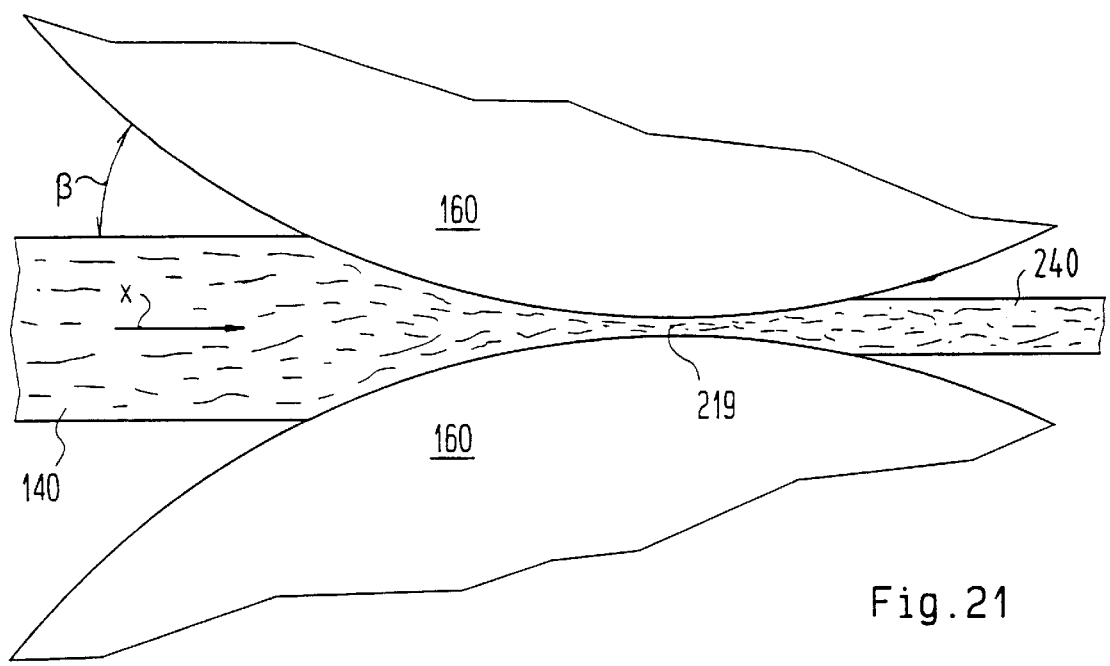
FIG. 21 shows a representation of the angle of engagement of the press disks into the fibre-material strand.

FIG. 21 shows an engagement angle β of 20° to 25° of a press disk 160, which was determined as the best possible for the pressing of the nonwoven strand 140, when a pressed strand 240 for the production of absorption bodies for feminine hygiene is to be produced from the folded nonwoven strand 140 consisting of natural fibres in FIG. 1.

The pressed strand 240 can be impregnated with a medium before the separation of absorption bodies 130. The liquid impregnation medium can be applied to the pressed strand 240 by spraying or by a dipping method. The liquid impregnation medium can be a water-repellant, like glycerine as a water-repellant impregnation medium. But, the impregnation medium can also be powdery. In this connection it should be understandable, that impregnated length portions of said pressed strand 240 can be used as sealing material.

Severing Station

The severing station D in FIG. 1 consists of at least two pairs of nip rollers 330, 332 which are arranged offset at 90° and can be respectively driven in opposition and which are arranged on both sides of the pressed strand 240. The nip rollers of the two pairs of nip rollers 330, 332 are each provided with a nipping boss 334, 336 and 338, 340. The nipping bosses 334, 336 reduce the cross-section between successive length portions of the pressed strand 240, which correspond approximately to the length of the absorption body 130, with the exception of a thin, axial connecting web not shown. This connecting web is severed by the last pair of nip rollers 332 and, as a result of the relatively high circumferential speed of the nip rollers 338, 340, corresponding to the conveying speed of the pressed strand 240, is ejected by means of a relatively strong axial momentum. During the nipping-off of the absorption body 130 by the pairs of nip rollers 330, 332, a front end 342 of the absorption body 130 is simultaneously preformed in a crude shape of a round hump 135, as can be seen from FIG. 1. In contrast, the rear end face of the absorption body 130 already has a preformed crude shape of a round finger dip 133. Said round humps 135 and round finger dips 133 can be moistened slightly after the severance of the connecting webs between successive absorption bodies 130 to add to finally smoothing at least said round humps 135 and, if desired, also said finger dips 133 of each absorption body 130 separated from the pressed strand 240.

If a wrapping band 82 is used, it is recommended to arrange at least one pair of cutting rollers as a cutting device at the end and/or at the start of the severing station D, so that the wrapping band 82 surrounding the pressed strand 240 and/or the thin, axial connecting web between successive portions of the pressed strand 240 can be cut through. The cutting rollers are not shown because they are generally known in the art.

FIG. 1 shows that, after severance, the absorption body 130 is transferred into an endless driving belt 344 which is continuously movable transversely to the direction of the arrow x and which is made narrower than the length of the absorption bodies 130. For receiving the absorption bodies 130, the driving belt 344 is provided with a multiplicity of U-shaped transverse grooves 346 which are each closed at the top by means of a driving cover 348 after the reception of the absorption body 130. The means for transferring the absorption bodies into the drivers belong to the state of the art and are therefore not shown.

Figure 22:
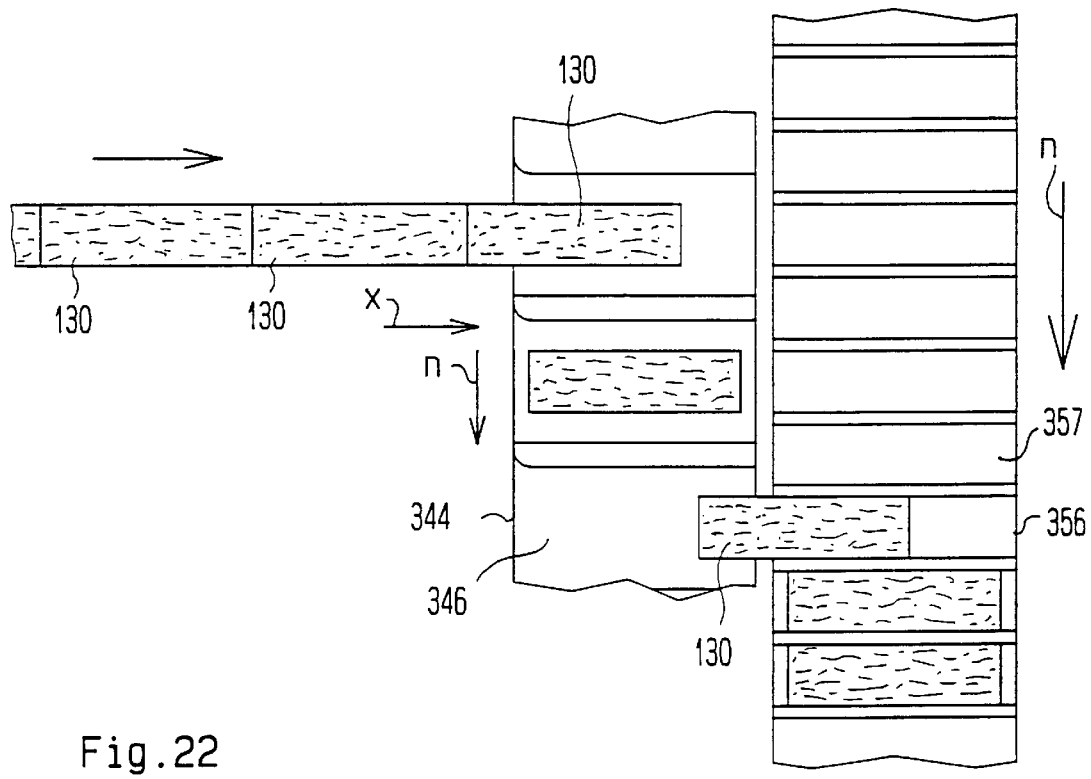
FIG. 22 shows a diagram of the transfer of the linearly produced absorption bodies onto a continuously rotating conveyor belt.

The transfer of the absorption bodies 130 out of the linear production of these according to FIG. 1 via the driving belt 344 onto a conveyor belt 356 is illustrated diagrammatically in FIG. 22. As already indicated in FIG. 1, the absorption bodies 130 are fed successively to the driving belt 344 which is driven continuously in the direction of the arrow n and which has the U-shaped transverse grooves 346, the width of which is made substantially larger than the diameter of the absorption bodies 130. Parallely arranged on the right of the driving belt 344 in FIG. 22 is the continuously drivable conveyor belt 356 provided with receptacles 357, the width of which is made only a little larger than the diameter of the absorption bodies 130. Arranged on the side of the driving belt 344 facing away from the conveyor belt 356 are accompanying pushing-over devices which are known per se and are therefore not shown and which are arranged coaxially to the transverse grooves 346 of the driving belt 344 and serve for transferring the absorption bodies 130 arranged in the transverse grooves 346 into the receptacles 357 of the conveyor belt 356, as shown in FIG. 22 with the aid of an absorption body 130 which is on the point of being transferred completely to a receptacle 357 of the conveyor belt 356.

The conveyor belt 356 has the job of feeding the absorption bodies to a hump-forming and finger-dip-forming station which is described below with reference to FIG. 23.

Hump-forming and finger-dip-forming station

Figure 23:
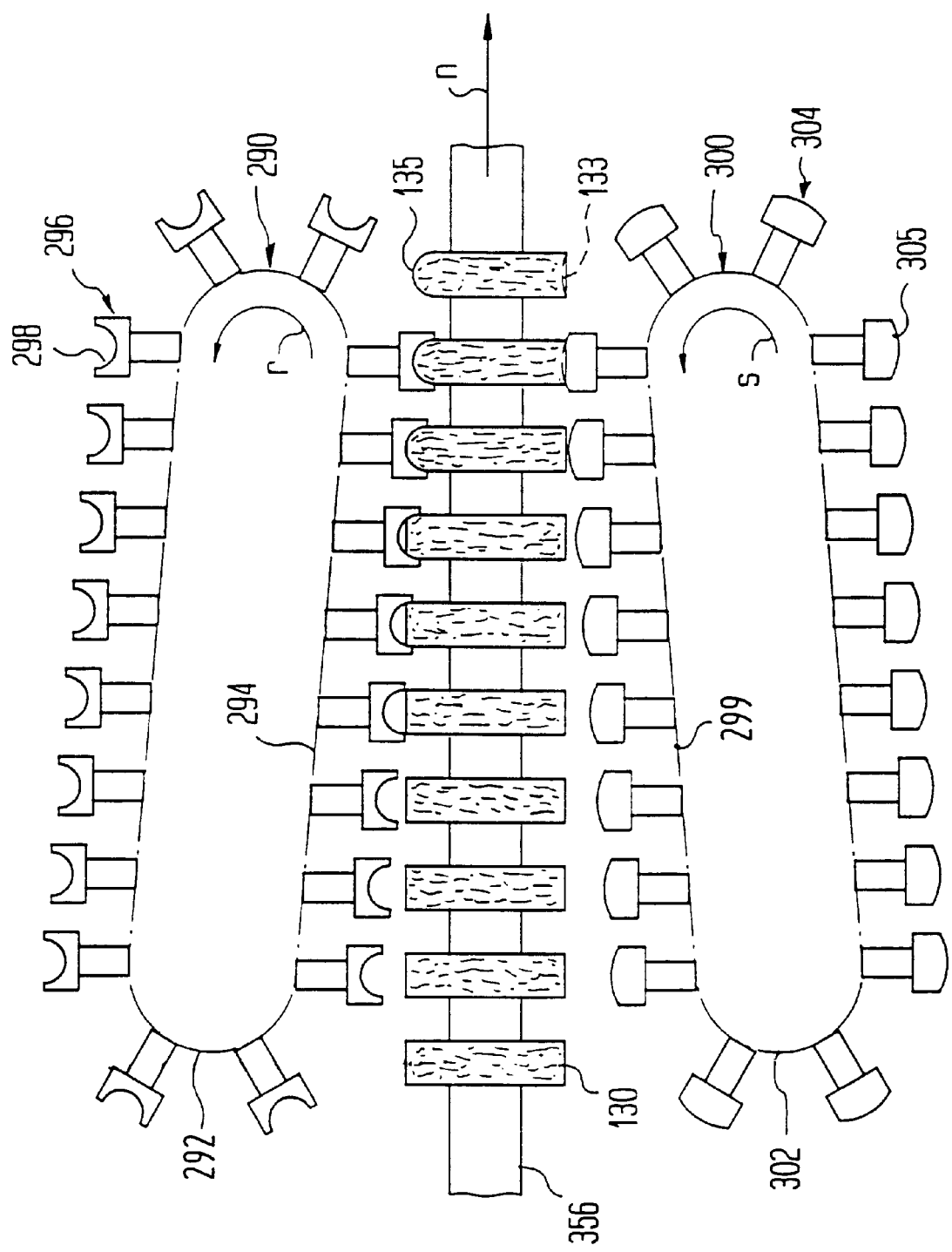
FIG. 23 shows a diagram of a rotary system for shaping the front and rear ends of absorption bodies.
Figure 25:
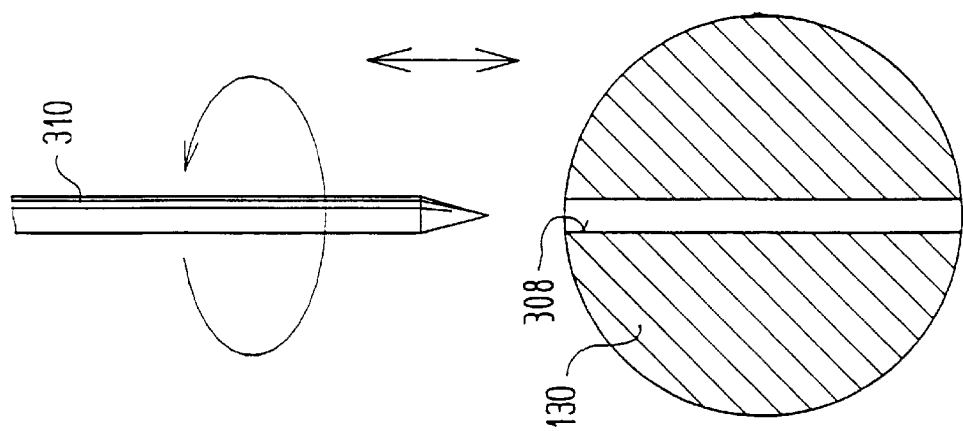
FIG. 25 shows a diagrammatic representation of a device for the pre-piercing of a diametral hole in absorption bodies for the attachment of a recovery tape.

The conveyor belt 356 movable in the direction of the arrow n, with absorption bodies 130 arranged on it, can be seen in FIG. 23. A rotary system 290 for smoothing humps 135 at the front end of the absorption bodies 130 constituting tampon blanks is provided on the side of this conveyor belt 356 which is on the left in the direction n. A further rotary system 300 for smoothing said finger dips 133 at the rear end of the absorption bodies 130 is arranged on the right-hand side of the conveyor belt 356 located opposite the rotary system 290 in the direction of the arrow n.

Although, the finally smoothing of the round humps 135 at the front end and, if it is desired, the round finger dips 133 at the rear end of each absorption body 130 separated from the pressed strand 240 may taken place by ultrasonic means or by ironing.

In both cases, the rotary system 290 can consist of an endless flexible member 292 which rotates in the direction of an arrow r in the anti-clockwise direction in a plane directed parallel to the plane of movement of the conveyor belt 356. A working side 294 forms, with the direction of movement n of the conveyor belt 356, an acute angle which closes in the direction n. In the present embodiment ironing means are used, which are rotating heatable forming dies 296 being fastened to the outside of the endless member 292. Said heatable forming dies 296 extend outwards from the conveyor belt 356 in the plane of movement of the conveyor belt 356 and are provided at their free ends, on the end face, with concave hemispherical forming heads 298 for the forming of convex hemispherical humps 135 at the front end of the absorption bodies 130. The forming dies 296 are fastened at equal spacings from one another corresponding to the spacings of the absorption bodies 130 which are arranged on the conveyor belt 356 at a distance from and parallel to one another transversely to the longitudinal direction of the latter. The forming dies 296 form, at least with the working side 294 of the conveyor belt 356, an acute angle opening in the direction of movement n of the conveyor belt 356, in such a way that each forming die 296 is located coaxially opposite the front end of an associated absorption body 130 on the conveyor belt 356. FIG. 23 shows that the working side 294 approaches the conveyor belt 356 in its direction of movement n in such a way that the spacing between the forming heads 298 and the front end of the absorption bodies 130 diminishes increasingly, until the forming heads 298 meet the front ends of the absorption bodies 130 and deform these into a round hump 135.

The rotary system 300 for forming finger dips 133 at the rear end of the absorption bodies 130 likewise consists of an endless flexible member 302 rotating in the clockwise direction s in a plane which is parallel to the direction of movement n of the conveyor belt 356. As is evident, the rotary system 300 is arranged mirror-symmetrically relative to the rotary system 290. Accordingly, at least one working side 299 of the member 302 is arranged at an acute angle to the conveyor belt 356 which, once again, closes in the direction n. Fastened to the outside of the endless member 302 are forming dies 304 which extend outwards in the plane of rotation of the endless member 302 and which, at their free ends, carry forming heads 305 having a convex forming face for forming the finger dips 133 in the rear end of each absorption body 130. For this purpose, here too, the forming dies 304 are respectively aligned coaxially, in the region of the working side 298, with the absorption bodies 130 transversely arranged in succession at a distance from one another on the conveyor belt 356. The arrangement of the forming dies 304 is such that these come to bear on the rear end of an absorption body 130 at the moment when a forming die 296 for forming the round hump 135 also comes to bear on the front end of the same absorption body 130. Consequently, the forming dies 296, 304 of the two rotary systems 290, 300 at the same time form abutments for one another, so that, even after the forming of the round hump 135 and of the finger dip 133, the absorption bodies 130 maintain their position on the conveyor belt 356.

Recovery-tape attachment station

Figure 24:
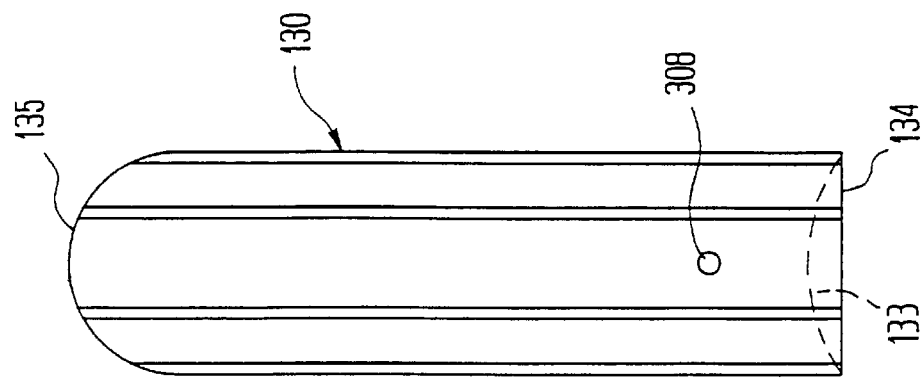
FIG. 24 shows a top view of an absorption body provided with a pre-pierced hole.
Figure 29:
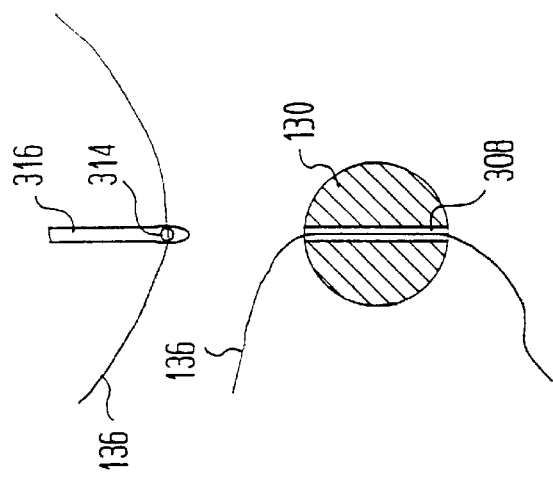
FIGS. 26, 27, 28 and 29 show four different work phases of a device for drawing in the recovery tape through the pre-drilled hole in the absorption body.

FIGS. 24 to 29 illustrate the operations which are carried out in the recovery-tape attachment station. FIG. 24 shows an absorption body 130 which is shaped to form a tampon and which, after the smoothing or ironing of the round hump 135 at the front end and of the finger dip 133 at the rear end of the absorption body 130, has been fed by means of the conveyor belt 356 to a recovery-tape attachment station. In this station, as mentioned, the tampon is provided with a hole 308 which, according to FIG. 24, extends at a distance of, for example, 6 mm from the rear end 134 of the absorption body 130 diametrically through the latter. According to FIG. 25, the attachment of this continuous hole 308 extending diametrically through the absorption body 130 is made by means of a rotating awl 310 which is movable to and fro diametrically relative to the absorption body 130 and which is driven in the direction of rotation. The tip, as a result of its rotation, at the same time forces the individual fibres in the absorption body 130 apart from one another carefully, without severing them. The diameter of the continuous pre-pierced hole 308 amounts, for example, to 0.6 mm.

Figure 26:
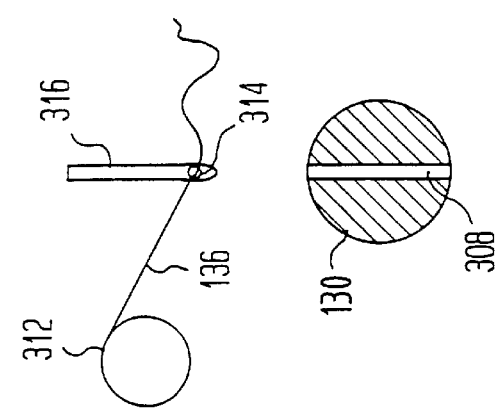

FIGS. 26 to 29 show individual work phases of the drawing of a recovery tape 136 into the hole 308 in the absorption body 130. In FIG. 26, the recovery tape 136 is guided from a stock reel 312 through an eye 314 of a needle 316 which is movable to and fro axially and which is a component of a rotary system, not shown, which is similar to that in FIG. 23 and by means of which the needle 316 is carried along synchronously with the movement of the absorption body 130 in the direction of movement of the conveyor belt 356. Consequently, during the continuous conveying movement of the needle 316 and the absorption body 130, the needle 316 can, according to FIG. 27, be guided through the hole 308 together with the recovery tape 136, a loose end 136a of the recovery tape 136 hanging down out of the needle eye 314 and, if appropriate, being brought into the effective range of a clamping device 318 by a suction device.

Figure 28:
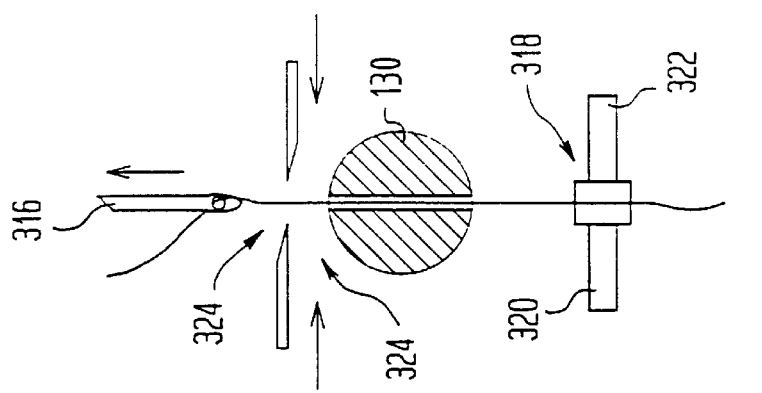
Figure 27:
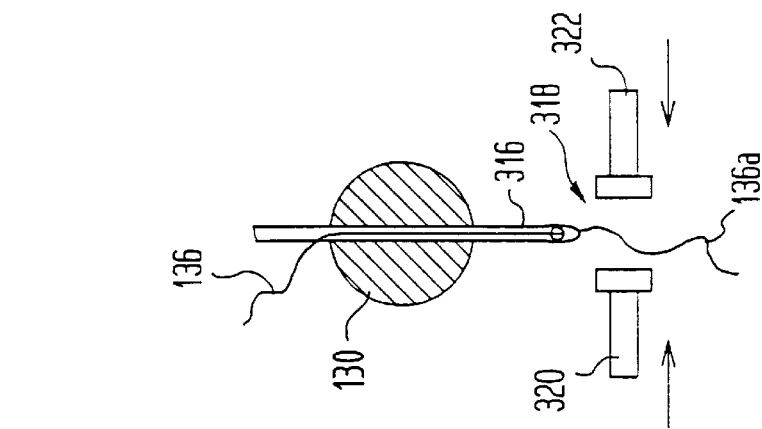

The clamping device 318 is, once again, a component of a rotary system and consists of two clamping jaws 320, 322 which are movable coaxially to and fro and which, in FIG. 27, are arranged at a distance from one another or form an interspace, into which the loose end 136a of the recovery tape 136 hangs down. In FIG. 28, the clamping jaws 320, 322 have been moved up against one another and have clamped the loose end 136a of the recovery tape 136 between them. As soon as this clamping operation has taken place, the needle 316 is drawn out of the absorption body 130. As FIG. 28 also shows, there is provided above the direction of movement of the absorption bodies 130 a severing device 324 which takes effect in a horizontal plane and which is likewise a component of the rotary system. After the needle 316 has been drawn back out of the absorption body 130, this severing device 324 is actuated, so that, according to FIG. 29, the recovery tape 136 is severed between the needle 316 and the absorption body 130. Thereafter, each absorption body 130, together with its recovery tape 136 drawn through the hole 308, is fed to a pneumatic knotting device known per se and therefore not shown. Simultaneously, the recovery tape 136 leading to the reel 312 is ready with its loose end 136a in the needle eye 314 for a renewed drawing-in operation.

Packaging Station

Figure 30:
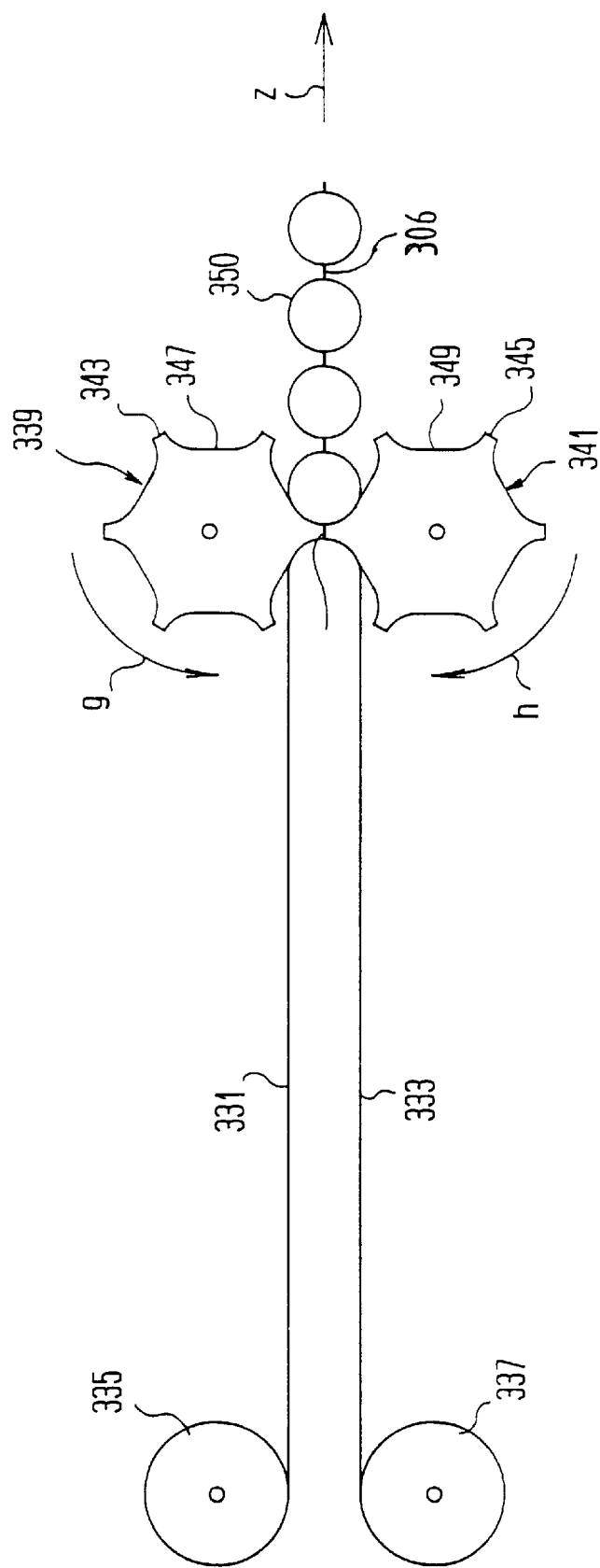

FIG. 30 illustrates a device for producing packaging pouches 350 from two plastic film strips 331, 333 which are each drawn off from a stock roll 335 and 337 in the direction of an arrow z. The two stock rolls 335, 337 are followed by two heated welding rollers 339, 341 which are drivable in the direction of rotation and which are arranged one above the other in a cross-sectional plane relative to the direction of transport z of the plastic film strips 331, 333. Each of the welding rollers 339, 341 is provided with welding ribs 343, 345 extending parallel to their axes, in such a way that, in the event of a synchronous rotational movement of the arrows g and h in opposite directions, the welding ribs 343, 345 of the two welding rollers 339, 341 are located respectively opposite one another and weld the film strips 331, 333 to one another along parallel seals 306. The welding ribs 343, 345 are, of course, separated from one another by equal circumferential angles of 60° in the present case, the interspaces between the successive welding ribs 343 and 345 having indentations 347, 349 which make it possible, by means of the two film strips 331, 333, to form the pouches 350, the cross-section of which is made somewhat larger than the cross-section of the absorption bodies 130.

FIG. 31 illustrates diagrammatically the packaging of the absorption bodies 130. The web welded together from the upper film strip 331 and the lower film strip 333 to form pouches 350 of a blister strip 351 is continuously driven parallel to and synchronously with a row of absorption bodies 130 in the direction of the arrows p, o parallel to one another, in such a way that the absorption bodies 130 come to rest coaxially to the pouches 350, of which the ends or bottoms 352 facing away from the absorption bodies 130 are closed by welding. Subsequently, the absorption bodies 130 produced as finished tampons 132 for feminine hygiene with a recovery tape 136 are pushed into the pouches 350 in the direction of an arrow q. Thereafter, the recovery tape 136 is attached in the form of a coil or spiral to the rear end 134 of each tampon 132, whereupon the projecting pouch edges 353 are folded against the rear ends 134 of the absorption bodies 130 positioned in the pouches 350 and are welded to one another in an air-tight manner. The blister pack produced in this way can, if required, be severed in the form of individual packs 355 by severance from the subsequent packs in the region of the welding seams 306 separating the packs, as indicated by the scissors shown in FIG. 31, or blister packs can be brought onto the market as multiple packs, from which the user can separate a pack in the region of the welding seams 306 each time as required, and for this case the welding seams 306 can have perforations.

List of Reference Symbols a arrow
b arrow
c arrow
d arrow
e arrow
f arrow
g arrow
h arrow
i arrow
n arrow
o arrow
p arrow
q arrow
r arrow
s clockwise direction
x direction of advance
z arrow A Folding station
B Wrapping-band attachment station
C Pressing station
D Severing station α acute angle
β angle of action I First folding operation
II Second folding operation
III Third folding operation
IV Fourth folding operation

38 stock roll
40 Nonwoven web
42 Guide plate
44 Endless conveyor belt
46 Stand part
48 Stand part
50 Baffle plate
52 Folding plate
54 Folding disk
56 Right-hand longitudinal side (nonwoven web 40)
58 Right-hand longitudinal edge
60 Left-hand longitudinal edge
62 First fold
64 Longitudinal fold
66 Four-layer bundle
68 Uncovered part (right-hand longitudinal side 56)
69 Six-layer bundle
70 Left-hand longitudinal side (nonwoven web 40)
72 Seven-layer nonwoven web
80 Stock roll
82 Wrapping band
84 Guide roller
86 Guide tube
88 Longitudinal slot (guide tube 86)
90 Endless conveyor belt
91 Support plate
92 Upper side
94 Driving roller
96 Deflecting roller
98 Introduction slot (guide tube 86)
100 dto.
102 Segment (guide tube 86)
104 dto.
106 dto.
108 Rear edge (segment 102)
110 Front edge (segment 104)
112 Rear edge (segment 104)
114 Front edge (segment 106)
116 Side tab (wrapping band 82)
118 dto.
120 Middle longitudinal slot (guide tube 86)
122 Closing device
124 Outer longitudinal edge (side tab 118)
126 Longitudinal edge (side tab 116)
128 Heat-sealing roller
130 Absorption body
131 Longitudinal grooves
132 Tampon
133 Finger dip
134 Rear end (tampon)
135 Round hump
136 Recovery tape
136a Loose end (recovery tape 136)
137 Knot
139 Longitudinal ribs
140 Nonwoven web (rounded, wrapped)
150 Disk press
151 Carrier plate (or bearing plate)
152 Passage orifice
153 Press axis
154 Tubular piece
156 Widened entry orifice
158 Longitudinal slots (catch nozzle 270)
160 Press disks
161 Bearing blocks
162 Supporting arms
164 Press-disk holders
166 Screw bolts
168 Screw nuts
170 Guide face in the form of a cylinder cutout
171 Holding plates
172 Stop face
174 Actuating device
176 Actuating bolt
178 Spur wheel
179 Transmission shaft
180 Bearing
182 Driving bevel wheel
184 Bevel-wheel disk
186 Press-disk body 188 Roller bearing
190 Axis
192 Bore (supporting arm 162)
194 Stepped annular face
196 Press-ring disk
198 Clamping ring
200 Electrical resistance-heating elements
202 Radial bores
204 Electrical line
206 Slip ring
208 Stationary sliding contact
210 Drive motor
212 Bracket
213 Reduction gear
214 Driving spur wheel
216 Internal toothing
218 Toothed ring
219 Press-disk gap
220 Bearing rollers
222 Transverse profile
224 Press-ring disk
226 Profile flanks
227 Press-ring disk
228 Annular grooves
229 Pressing edge (press-ring disk 227)
230 Adjusting device
231 Corrugations
232 Control ring
233 Circular groove
234 Control bolt
236 Control groove
238 Supporting face
240 Pressed strand
241 Arrangement
242 Longitudinal mid-axis
244 Countersunk bore
246 Threaded bores
248 Adjusting screws
250 Cone tips
252 Guides
253 Guide tongues
254 Long holes
255 Tongue-and-groove connection
256 V-shaped transverse groove
257 Supporting face
258 Longitudinal mid-axis
259 Screw connection
260 Transverse profile
261 Profile flanks
262 Pressing edge (press-ring disk 196)
263 Side faces
265 End faces
268 Supply nozzle
270 Catch nozzle
273 Conical widening
274 Middle length portion
275 Cylindrical end portion
276 End portion
278 Resistance-heating element
282 Pressed-strand core
290 Rotary system
292 Flexible member (rotary system 290)
294 Working side
296 Forming dies
298 Forming heads
299 Working side
300 Rotary system
302 Endless flexible member (rotary system 300)
304 Forming dies
305 Forming heads
306 welding seam
308 Hole
310 Awl
312 Stock reel
314 Eye
316 Needle
318 Clamping device
320 Clamping jaw
322 Clamping jaw
324 Severing device
330 Pair of nip rollers
331 Film strip
332 Pair of nip rollers
333 Film strip
334 Nipping boss
335 Stock rolls
336 Nipping boss
337 Stock rolls
338 Nipping boss
339 Welding rollers
340 Nipping boss
341 Welding rollers
342 Front end (absorption body 130)
343 Welding ribs
344 Carrier belt
345 Welding ribs
346 Transverse grooves
347 Indentations
348 Driving cover
349 Indentations
350 Packaging pouches
351 Blister strip
352 Ends or bottoms (packaging pouches 350)
353 Nipping groove
355 Individual packs
356 Conveyor belt
357 Receptacles (conveyor belt 356)

I claim:

1. Apparatus for the production of longitudinally extending pressed absorption bodies, having a front end and a rear end, from an endless nonwoven web comprising a carrier plate provided with a passage orifice, in which is arranged a tubular piece having a widened entry orifice and provided with a plurality of slots extending in the longitudinal direction, with a disk press having a plurality of circular press disks, an outer circumferential portion of which projects respectively through a slot into the interior of the tubular piece, the press disks being mounted rotatably on axles fastened on press-disk holders which are arranged on the carrier plate at angular spacings in a common plane perpendicular to the tubular piece and which are adjustable radially relative to the tubular piece, wherein an apparatus for forming an endless nonwoven web precedes the tubular piece, an exit orifice of which is arranged at a distance in front of a gap formed by the press disks, there being provided a drive device for synchronously driving the press disks, so that the nonwoven web can be drawn by the press disks into the press-disk gap and can simultaneously be pressed radially at least to a final diameter of a pressed strand in a single operation.

2. Apparatus of claim 1 wherein eight or more press disks are arranged at equal circumferential angular spacings about a press axis residing within the passage orifice.

3. Apparatus of claim 1 wherein the press-disk holder are respectively provided at their radially inner end with supporting arms, each of the supporting arms having one of the essentially circular press disks mounted on a radially inner end so as to be drivable about its axis in the direction of rotation.

4. Apparatus of claim 1 wherein a transverse profile of each press disk is widened radially inwards in a V-shaped manner, flanks of the profile of each press disk forming an acute angle an merging into parallel side faces at a radial distance removed from the pressing edge.

5. Apparatus of claim 1 wherein the tubular piece is mounted on an entry side of the disk press, a free cross-section of said tubular piece being narrowed in the form of a supply nozzle at a front end.

6. Apparatus of claim 1 wherein a catch nozzle for the pressed strand is arranged at a distance behind the press-disk gap proximal a conveying direction.

7. Apparatus of claim 6 wherein the nonwoven strand forms an engagement angle of 20° to 25° with the press disk for the pressing of the nonwoven strand.

8. Apparatus of claim 7 which further comprises a severing station comprising at least two pairs of nip rollers which are arranged offset at 90° at both sides of the pressed strand and respectively drivable in opposition.

9. Apparatus of claim 8 wherein the nip rollers of said at least two pairs of nip rollers are each provided with a nipping boss to reduce the cross-section between successive length portions of the pressed strand with the exception of a thin, axial connecting web.

10. Apparatus of claim 1 which further comprises a rotary system for forming humps at the front end of the absorption bodies constituting tampon blanks provided on one side of a conveyor belt, and comprising a further rotary system for forming finger dips at the read end of the absorption bodies arranged on the other side of the conveyor belt located opposite the rotary system.

11. Apparatus of claim 10 wherein said rotary system comprises a first endless flexible member which rotates in an anti-clockwise direction in a plane directed parallel to a plane of movement of the conveyor belt, a working side of said first endless flexible member forming, with the direction of movement of the conveyor belt, an acute angle closing in the direction, rotating heatable forming dies which extend outwards form the conveyor belt in the plane of movement of the conveyor belt, the dies having concave hemispherical forming heads thereon, for the forming of said convex hemispherical humps at the front end of the absorption bodies.

12. Apparatus of claim 10 wherein the rotary system for forming finger dips at the rear end of the absorption bodies comprises a second endless flexible member rotating in the clockwise direction in a plane which is parallel to the direction of movement of the conveyor belt.

13. Apparatus of claim 12 wherein a recovery string attachment station is associated with the conveyor belt and comprises a rotating awl which is movable to and fro diametrically relative to the absorption body for piercing a diametrical hole in the rear end of each absorption body.

14. Apparatus of claim 1 which further comprises a device for producing packaging pouches from two film strips which are each drawn off from a stock roll being followed by two heated welding rollers which are drivable in the direction of rotation and which are arranged one above the other in a cross-sectional plane relative to the direction of transport of the film strips.

15. The apparatus of claim 1 wherein the synchronously driven press disks can simultaneously press the strand to the final diameter in a single operation.

16. A process for the production of longitudinally extending pressed absorption bodies from an endless nonwoven web comprising the steps of:

a) rotating a plurality of pressing elements which are substantially arranged and configured in a plane at a single pressing station;

b) driving the nonwoven web in a first direction, substantially perpendicular to the plane of the pressing elements through the rotating plurality of pressing elements, wherein the nonwoven web is compressed simultaneously with the plurality of pressing elements to its final dimension in a single operation, to form a substantially cylindrical pressed strand having at least three longitudinal grooves and a correspondingly number of ribs therebetween arranged at substantially equal angular spacings about the circumference of the cylindrical form; and c) subdividing the pressed strand into portions of specific length.

17. The process of claim 16 further comprising the step of impregnating the pressed strand with a medium before the separation of absorption bodies.

18. The process according to claim 16 wherein the absorption body is formed as a tampon.

19. The process of claim 16 wherein longitudinal grooves of differing depth are pressed into the nonwoven web.

20. The process of claim 16 wherein radial outer portions of the grooves are substantially closed to impart a substantially cylindrical surface to the processed strand.

21. The process of claim 16 wherein the step of subdividing the pressed strand into portions comprises first nip-rolling the pressed strand in a manner to substantially reduce the cross-section between the successive length portions while leaving an axial connecting web between the portions, and thereafter severing the connecting web with a second nip-rolling, the first and second nip-rolling being offset in steps of 90°.

22. The process of claim 16 further comprising the steps of forming a domed front end of each absorption body and a depression in a rear end of each absorption body.

23. The process of claim 18 wherein a rear end of the tampon is provided, during its conveyance, with a recovery string.

24. The process of claim 23 wherein the recovery string is drawn in through a pre-pierced hole by means of a needle having a closed eye, a loose end of the recovery string is clamped, and subsequently the needle is drawn back, whereupon, to draw in a recovery string length completely, the recovery string is severed in an adjustable position above the tampon, whilst a sufficiently long end simultaneously remains threaded through the needle so as to be ready for the next tampon.

25. The process according to claim 22 wherein the step of forming a domed front end on a first absorption body occurs simultaneously with the step of forming a depressed rear end in an adjacent absorption body.

26. The process of claim 17 wherein the impregnation medium is liquid.

27. The process of claim 26 wherein the liquid impregnation medium is water-repellant.

28. The process of claim 16 further comprising the steps of folding the nonwoven web several times onto itself, parallel to the longitudinal direction, from one longitudinal edge to form a multi-layered nonwoven web portion, then folding the other longitudinal edge onto the multi-layer nonwoven web portion.

29. The process of claim 28 further comprising the step of wrapping the folded web with a fluid-permeable wrapping band.

* * * * *